US012788890B2

(12) United States Patent
Carlsson et al.

(10) Patent No.: US 12,788,890 B2
(45) Date of Patent: Nov. 10, 2026

(54) SYRINGE CARRIERS

(71) Applicant: SHL MEDICAL AG, Zug (CH)

(72) Inventors: Daniel Carlsson, Enskede (SE); Ming-Ting Yin, Taoyuan City (TW); Anders Boström, Ingaro (SE); Chia-Hsin Su, New Taipei City (TW); Meng-Jhen Chiou, Taoyuan City (TW)

(73) Assignee: SHL Medical AG, Zug (CH)

( * ) Notice: Subject to any disclaimer, the term of this patent is extended or adjusted under 35 U.S.C. 154(b) by 635 days.

(21) Appl. No.: 18/275,337

(22) PCT Filed: Dec. 21, 2021

(86) PCT No.: PCT/EP2021/086939
§ 371 (c)(1),
(2) Date: Aug. 1, 2023

(87) PCT Pub. No.: WO2022/171342
PCT Pub. Date: Aug. 18, 2022

(65) Prior Publication Data

US 2024/0115808 A1 Apr. 11, 2024

Related U.S. Application Data

(60) Provisional application No. 63/178,577, filed on Apr. 23, 2021, provisional application No. 63/162,601,
(Continued)

(30) Foreign Application Priority Data

Jul. 23, 2021 (EP) .................................... 21187327

(51) Int. Cl.
*A61M 5/24* (2006.01)
*A61M 5/32* (2006.01)

(52) U.S. Cl.
CPC ............ *A61M 5/24* (2013.01); *A61M 5/3202* (2013.01); *A61M 2005/2403* (2013.01); *A61M 2005/2437* (2013.01)

(58) Field of Classification Search
CPC ........ A61M 5/24; A61M 5/3202; A61M 5/20; A61M 2005/2403; A61M 2005/2437;
(Continued)

(56) References Cited

U.S. PATENT DOCUMENTS 3,144,178 A 8/1964 Sarnoff
5,078,698 A 1/1992 Stiehl et al.
(Continued)

FOREIGN PATENT DOCUMENTS

EP 2601992 A1 6/2013
EP 3153196 A1 4/2017
(Continued)

OTHER PUBLICATIONS

International Search Report and Written Opinion for Int. App. No. PCT/EP2021/086939, mailed Apr. 25, 2022.

*Primary Examiner* — Laura A Bouchelle
*Assistant Examiner* — Sarah Dympna Grasmeder
(74) *Attorney, Agent, or Firm* — McDonnell Boehnen Hulbert & Berghoff LLP

(57) ABSTRACT

Syringe carriers for medicament delivery devices are described where a medicament delivery device sub-assembly extending along a longitudinal axis from a proximal end to a distal end is described having a tubular housing, a tubular syringe carrier inside the housing and a syringe inside the syringe carrier. The syringe includes a needle shield and a medicament container comprising a shoulder. The housing includes a flexible arm extending in the axial direction relative to the longitudinal axis, the flexible arm having an inwardly extending protrusion arranged in a gap
(Continued)

between the shoulder and the needle shield. The syringe carrier has a proximal portion and a distal portion, and the proximal portion is arranged adjacent to the flexible arm of the housing so that movement of the flexible arm of the housing in a radial direction relative to the longitudinal axis is restricted by the proximal portion of the syringe carrier.

7 Claims, 20 Drawing Sheets

Related U.S. Application Data filed on Mar. 18, 2021, provisional application No. 63/158,580, filed on Mar. 9, 2021, provisional application No. 63/153,408, filed on Feb. 25, 2021, provisional application No. 63/149,380, filed on Feb. 15, 2021.

(58) Field of Classification Search
CPC .. A61M 2005/2407; A61M 2005/2418; A61M 2005/244
See application file for complete search history.

(56) References Cited

U.S. PATENT DOCUMENTS

| | | | | |
|---|---|---|---|---|
| 5,514,097 | A | 5/1996 | Knauer | |
| 5,681,291 | A | 10/1997 | Galli | |
| 7,004,929 | B2 | 2/2006 | McWethy et al. | |
| 8,048,029 | B2 | 11/2011 | Gillespie, III et al. | |
| 8,672,901 | B2 | 3/2014 | Bollenbach et al. | |
| 8,801,679 | B2 | 8/2014 | Iio et al. | |
| 9,186,462 | B2 | 11/2015 | Lanzi et al. | |
| 9,289,554 | B2 | 3/2016 | Hourmand et al. | |
| 9,408,970 | B2 | 8/2016 | Hourmand et al. | |
| 9,572,937 | B2 | 2/2017 | Ekman et al. | |
| 9,713,678 | B2 | 7/2017 | Hourmand et al. | |
| 9,789,254 | B2 | 10/2017 | McLoughlin et al. | |
| 9,867,940 | B2 | 1/2018 | Holmqvist et al. | |
| 10,265,475 | B2 | 4/2019 | Newton et al. | |
| 10,300,202 | B2 | 5/2019 | Dasbach et al. | |
| 10,342,925 | B2 | 7/2019 | McLoughlin et al. | |
| 10,441,719 | B2 | 10/2019 | Hourman et al. | |
| 10,478,560 | B2 | 11/2019 | Lesch | |
| 10,881,799 | B2 | 1/2021 | Hirschel et al. | |
| 10,918,803 | B2 | 2/2021 | Kemp et al. | |
| 2007/0173770 | A1 | 7/2007 | Stamp | |
| 2009/0012471 | A1 | 1/2009 | Harrison | |
| 2010/0152655 | A1 | 6/2010 | Stamp | |
| 2011/0172602 | A1 | 7/2011 | Eaton | |
| 2012/0053528 | A1 | 3/2012 | Bollenbach | |
| 2013/0184655 | A1 | 7/2013 | Lanzi et al. | |
| 2014/0323985 | A1 | 10/2014 | Hourmand et al. | |
| 2015/0045734 | A1 | 2/2015 | McLoughlin et al. | |
| 2015/0119809 | A1 | 4/2015 | Loof | |
| 2016/0228648 | A1 | 8/2016 | Goraltchouk et al. | |
| 2016/0263325 | A1 | 9/2016 | Huthmacher et al. | |
| 2017/0007763 | A1 | 1/2017 | McLoughlin et al. | |
| 2017/0216527 | A1 | 8/2017 | Lesch | |
| 2017/0258998 | A1 | 9/2017 | Stamp | |
| 2017/0259000 | A1 | 9/2017 | Dyer et al. | |
| 2018/0008776 | A1 | 1/2018 | Ogawa et al. | |
| 2018/0028756 | A1 | 2/2018 | Maxfield | |
| 2018/0104413 | A1 | 4/2018 | McLoughlin et al. | |
| 2018/0140782 | A1 | 5/2018 | Kemp et al. | |
| 2018/0169338 | A1 | 6/2018 | Mosebach et al. | |
| 2019/0060579 | A1 * | 2/2019 | Daniel | A61M 5/3202 |
| 2019/0201629 | A1 | 7/2019 | Hourmand et al. | |
| 2019/0217021 | A1 | 7/2019 | Maxfield | |
| 2019/0224416 | A1 | 7/2019 | Dugand et al. | |
| 2019/0290849 | A1 | 9/2019 | Hirschel et al. | |
| 2020/0282152 | A1 | 9/2020 | Hezkiahu | |
| 2020/0316303 | A1 | 10/2020 | Folk et al. | |
| 2020/0330676 | A1 | 10/2020 | Klitmose et al. | |
| 2020/0397993 | A1 | 12/2020 | Stamp | |
| 2020/0405960 | A1 | 12/2020 | Hourmand et al. | |
| 2021/0077743 | A1 | 3/2021 | Kemp et al. | |
| 2021/0353860 | A1 * | 11/2021 | Garson | A61M 5/20 |

FOREIGN PATENT DOCUMENTS

| | | | |
|---|---|---|---|
| EP | 3153197 | A1 | 4/2017 |
| EP | 2654843 | B1 | 9/2018 |
| EP | 2734256 | B1 | 12/2018 |
| EP | 2788052 | B1 | 4/2019 |
| EP | 3302642 | B1 | 9/2019 |
| EP | 3695863 | A1 | 8/2020 |
| EP | 2788050 | B1 | 11/2020 |
| EP | 3785749 | A1 | 3/2021 |
| EP | 3791908 | A1 | 3/2021 |
| EP | 3177346 | B1 | 6/2021 |
| EP | 3484556 | B1 | 7/2023 |
| WO | 2005/115507 | A1 | 12/2005 |
| WO | 2007/083115 | A1 | 7/2007 |
| WO | 2010/097116 | A1 | 9/2010 |
| WO | 2013/083615 | A1 | 6/2013 |
| WO | 2014/060215 | A1 | 4/2014 |
| WO | 2016/193341 | A1 | 12/2016 |
| WO | 2016/193374 | A1 | 12/2016 |
| WO | 2017/071909 | A1 | 5/2017 |
| WO | 2018/011256 | A1 | 1/2018 |
| WO | 2018/015119 | A1 | 1/2018 |
| WO | 2019/068109 | A1 | 4/2019 |
| WO | 2019/081578 | A1 | 5/2019 |
| WO | 2019/126421 | A1 | 6/2019 |
| WO | 2019/185335 | A1 | 10/2019 |
| WO | 2019/224784 | A1 | 11/2019 |
| WO | 2019/224785 | A1 | 11/2019 |
| WO | 2020/064572 | A1 | 4/2020 |
| WO | 2020/164910 | A1 | 8/2020 |
| WO | 2021/008839 | A1 | 1/2021 |
| WO | 2021/115706 | A1 | 6/2021 |

* cited by examiner

Figure 9
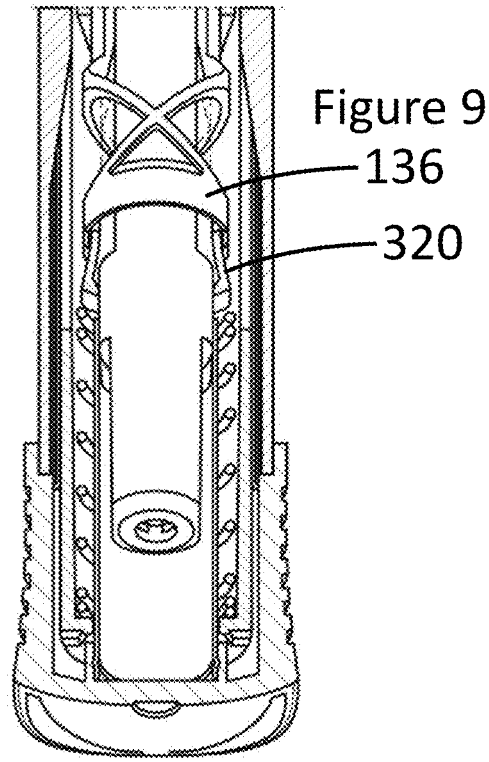
Figure 10
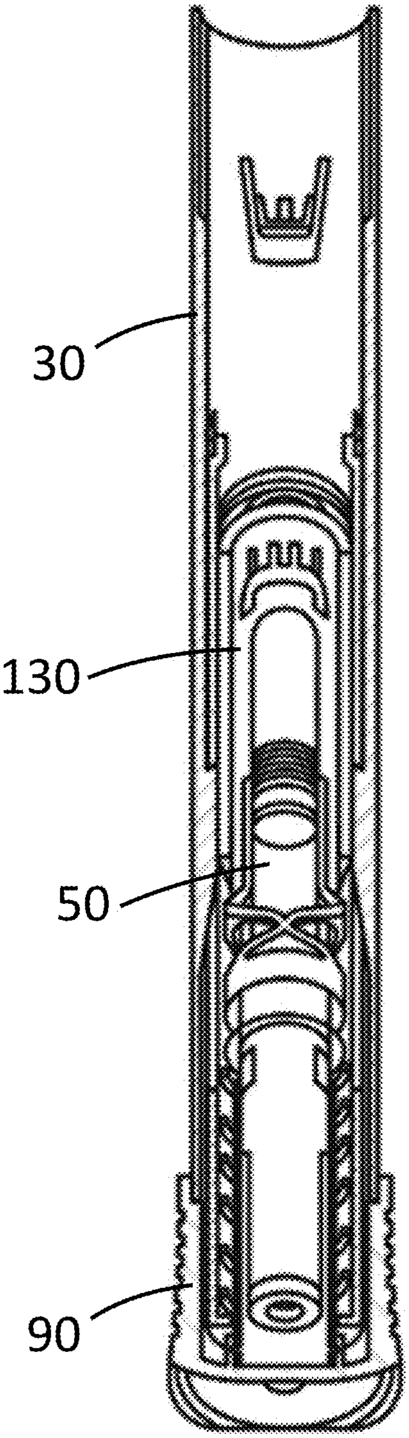
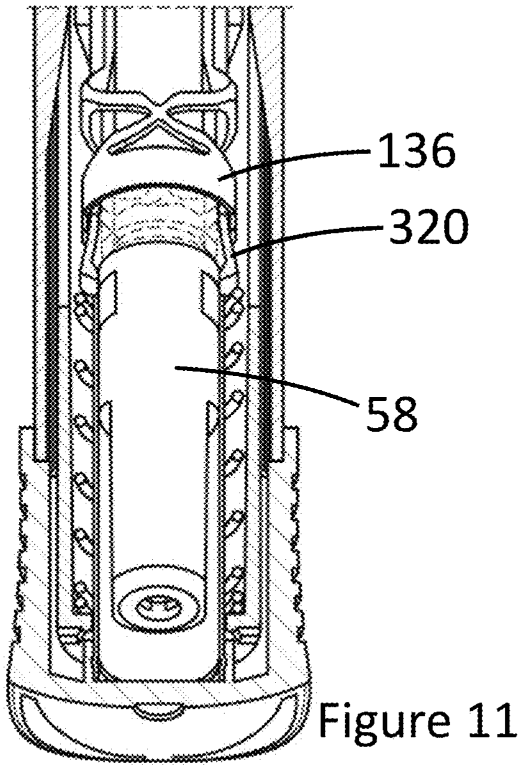
Figure 11

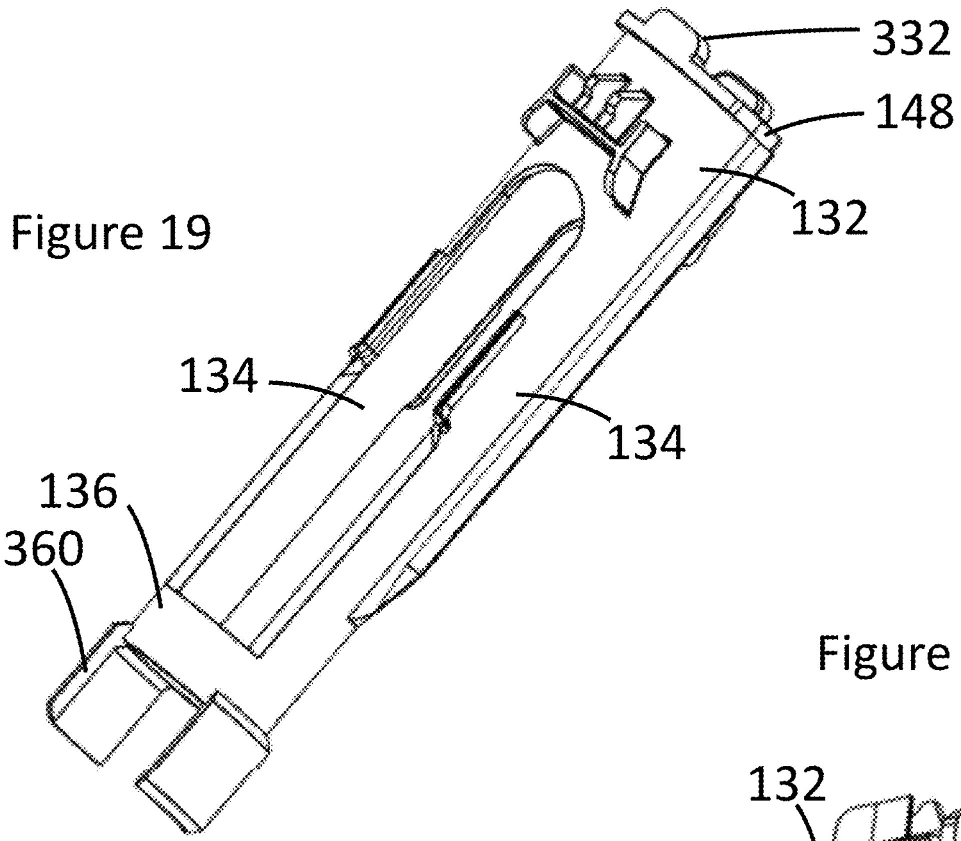
Figure 19
Figure 20
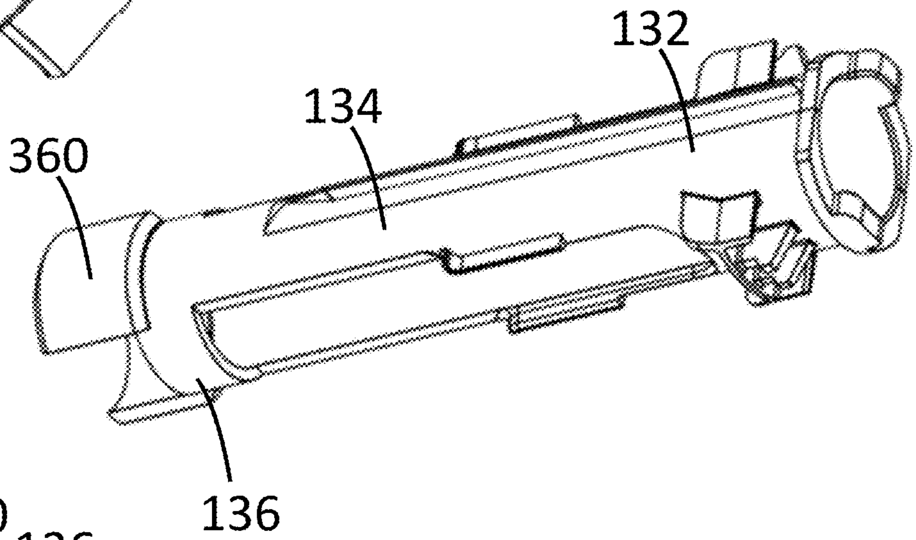
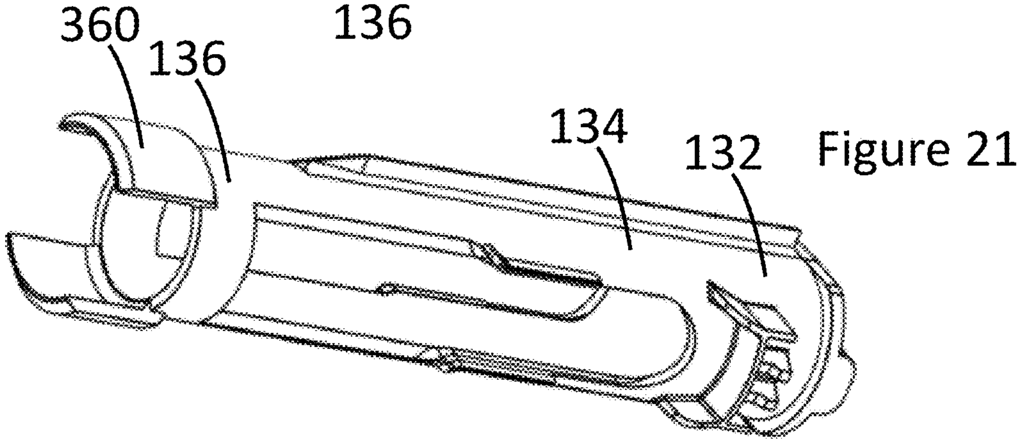
Figure 21

Figure 31
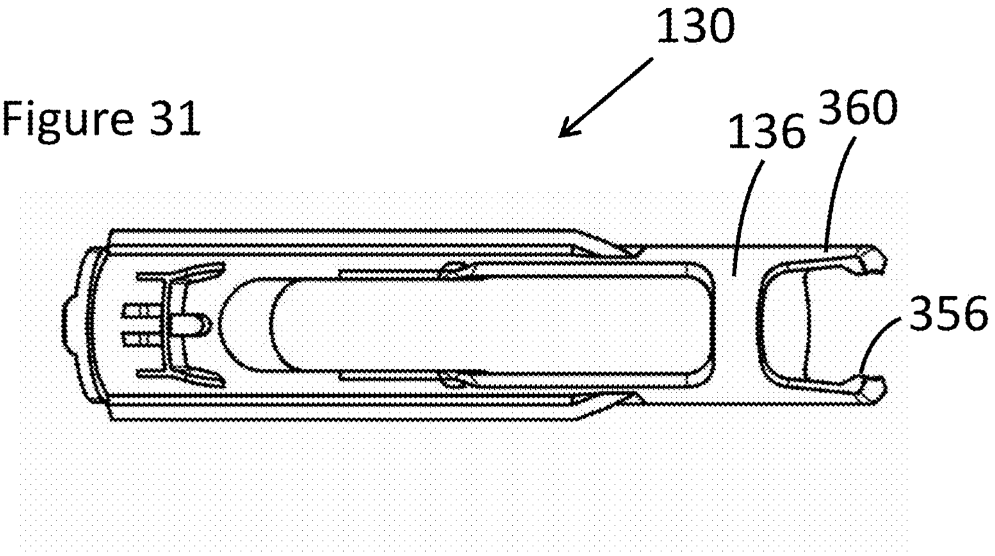
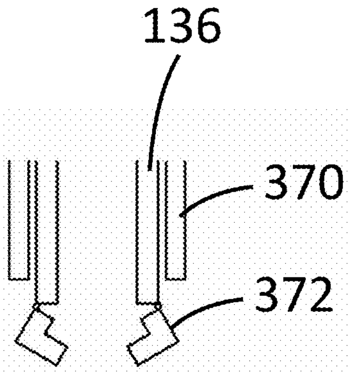
Figure 32
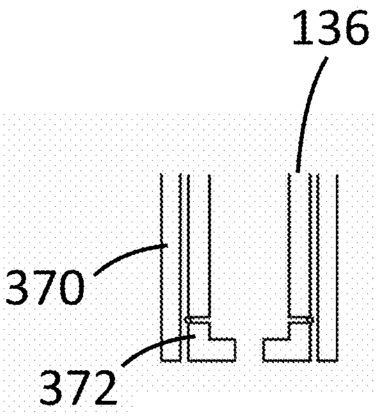
Figure 33
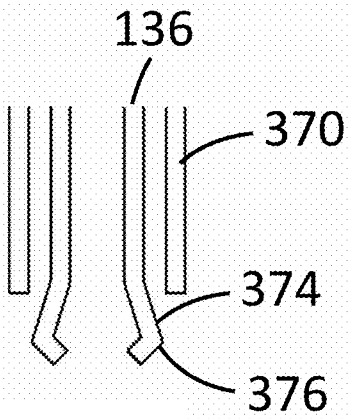
Figure 34
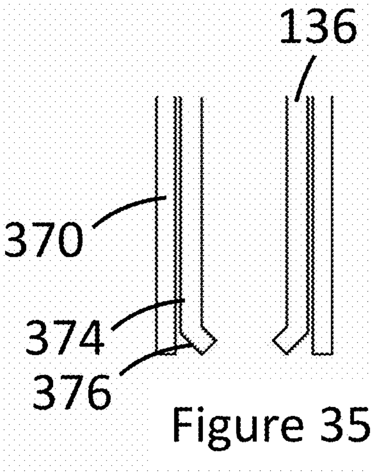
Figure 35

Figure 42
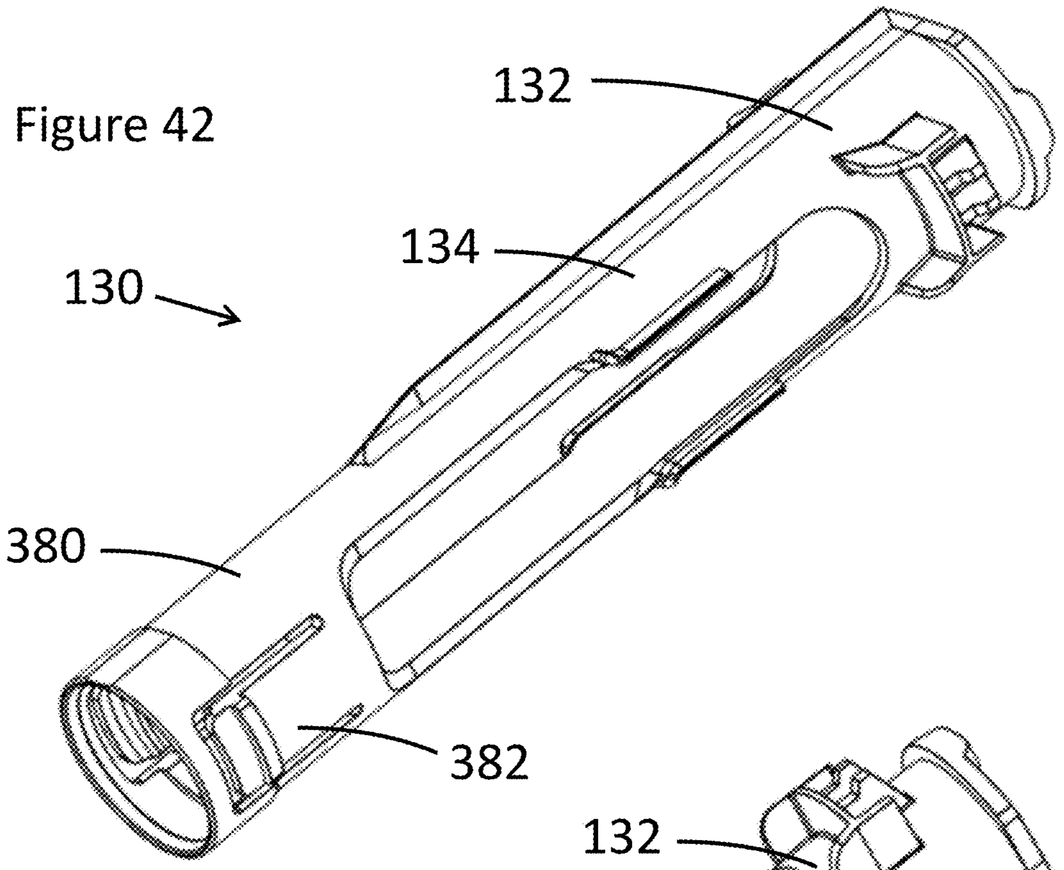
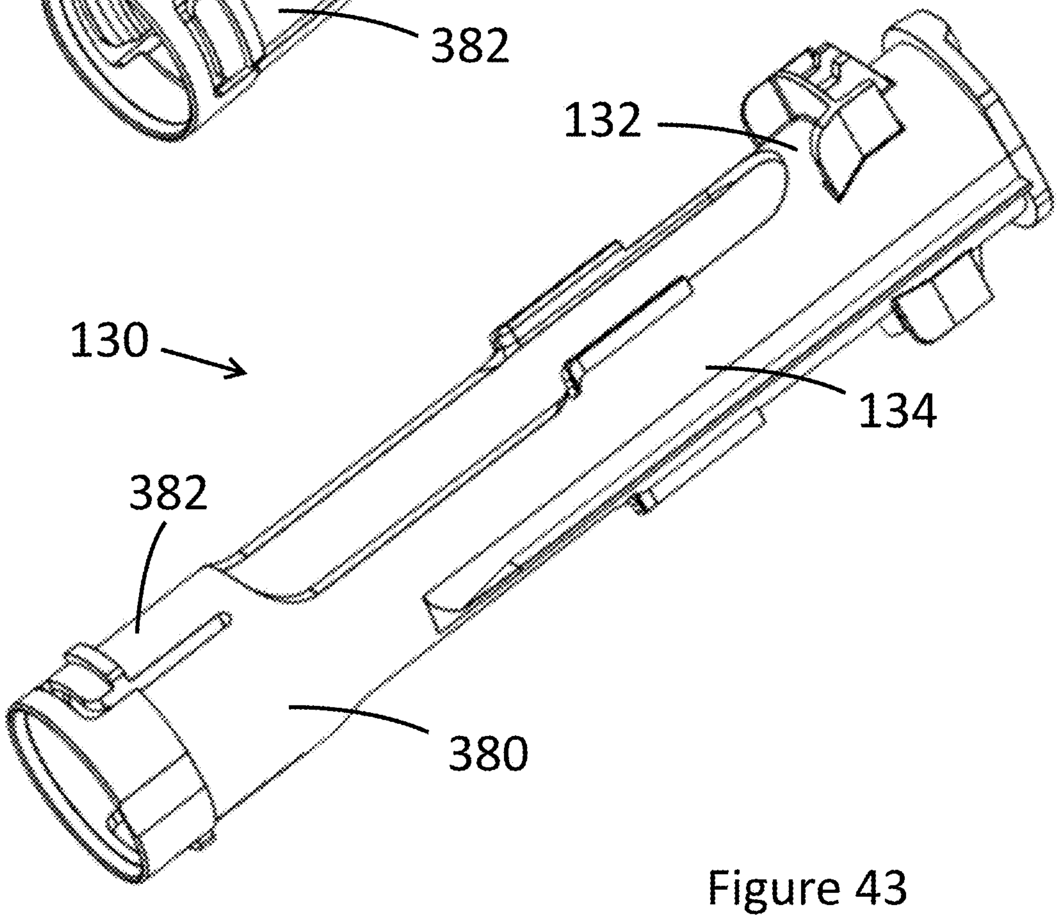
Figure 43

Figure 46
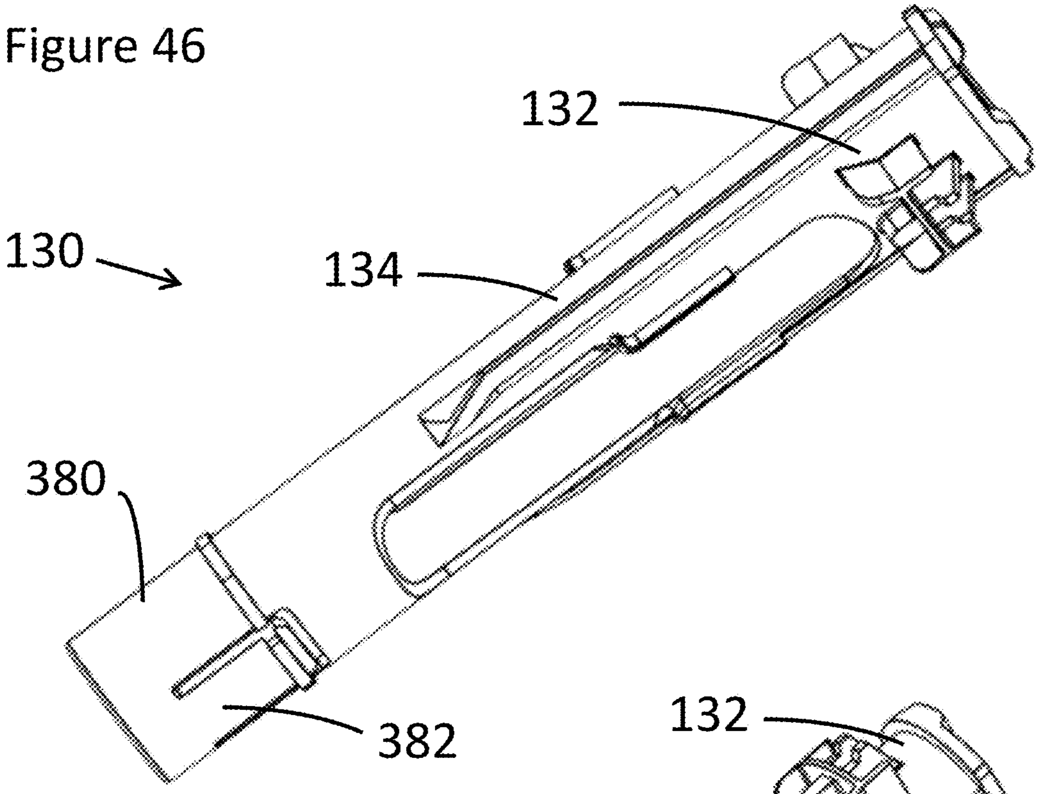
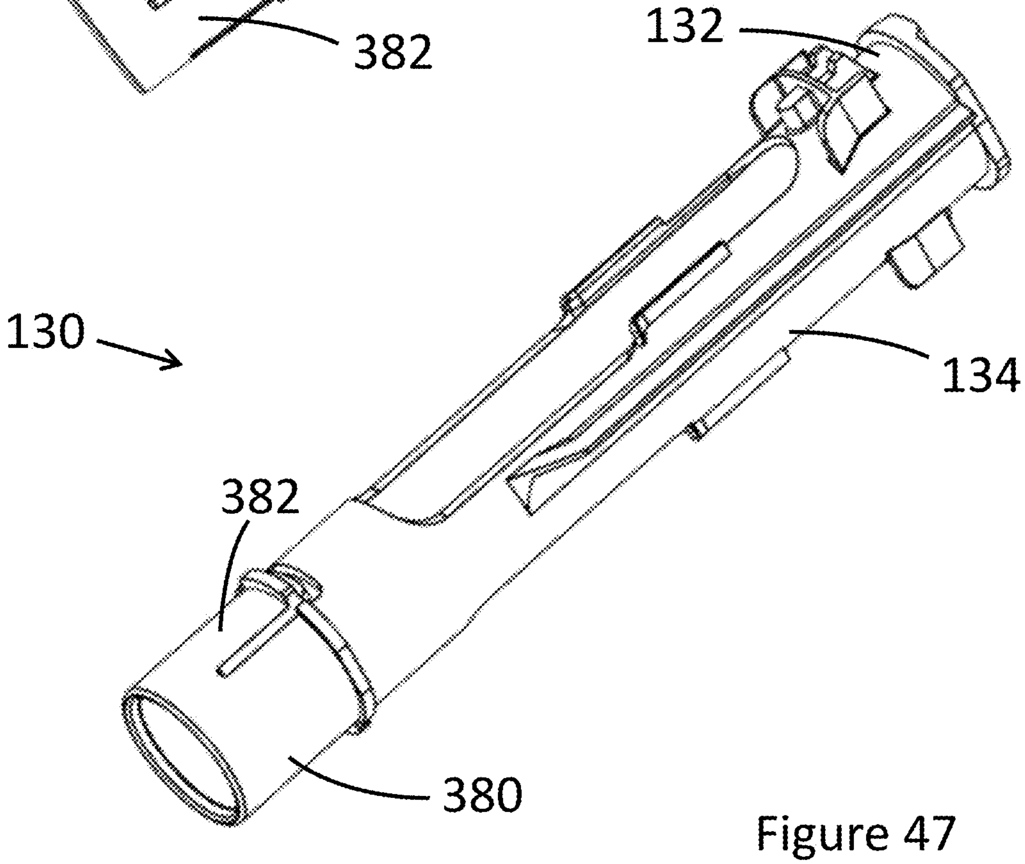
Figure 47

Figure 48
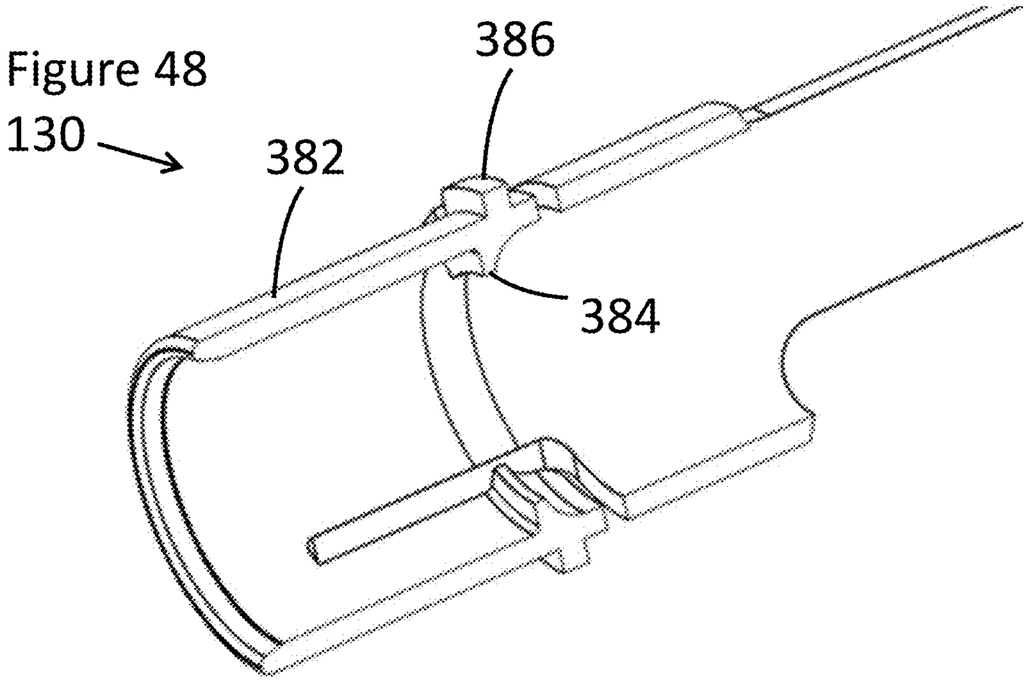
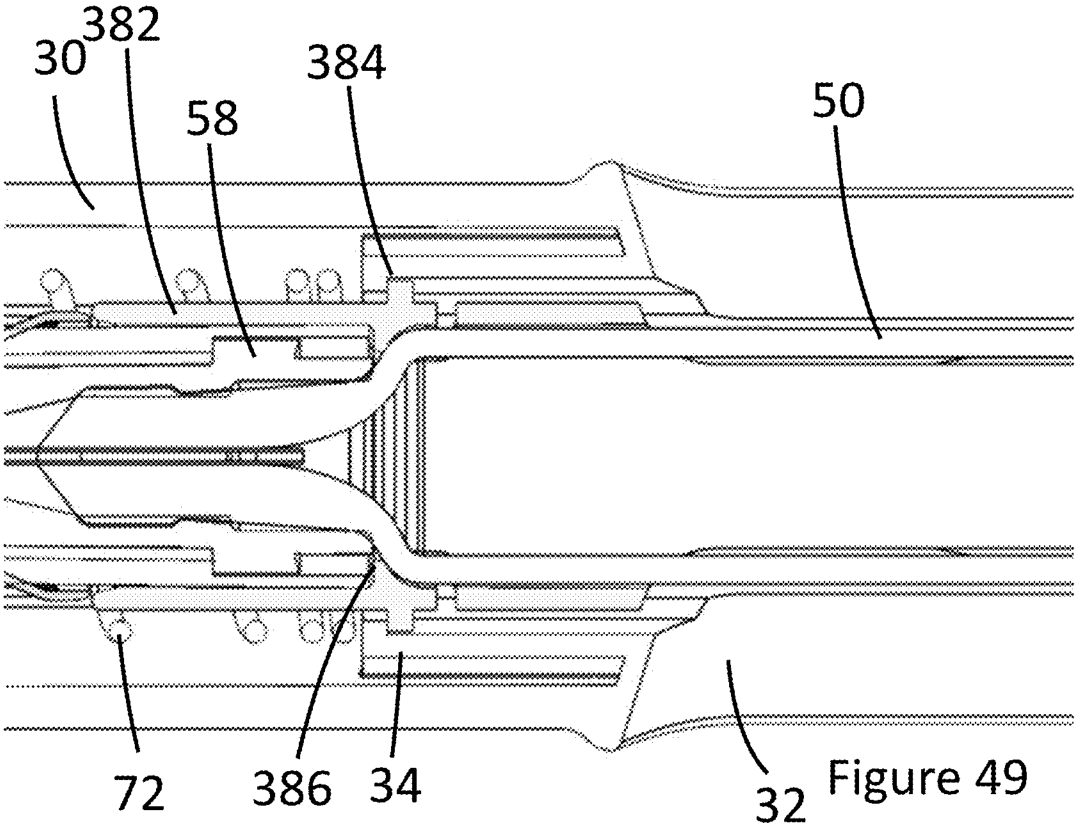
Figure 49

Figure 50
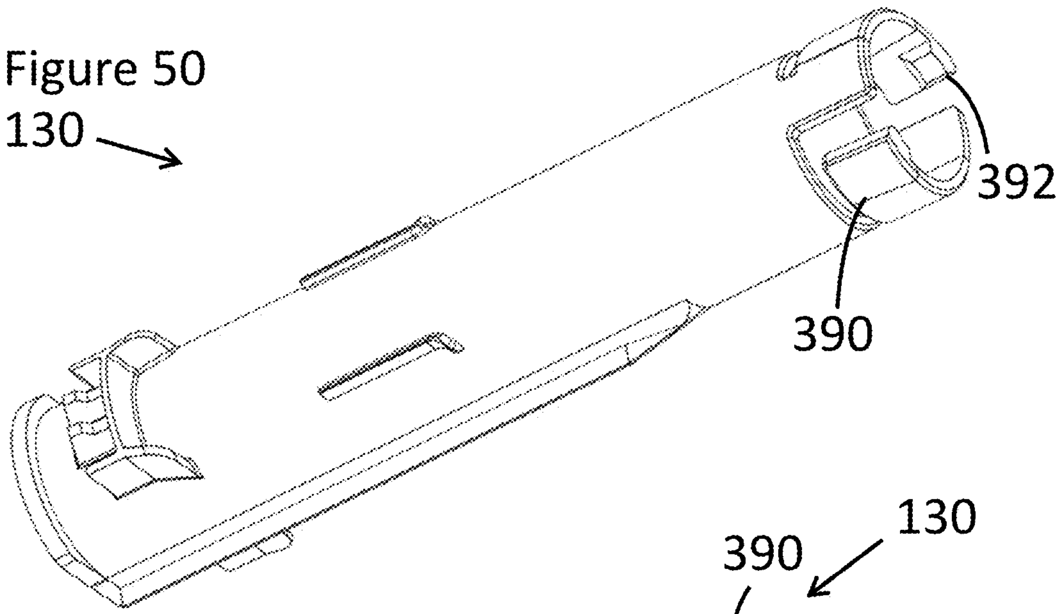
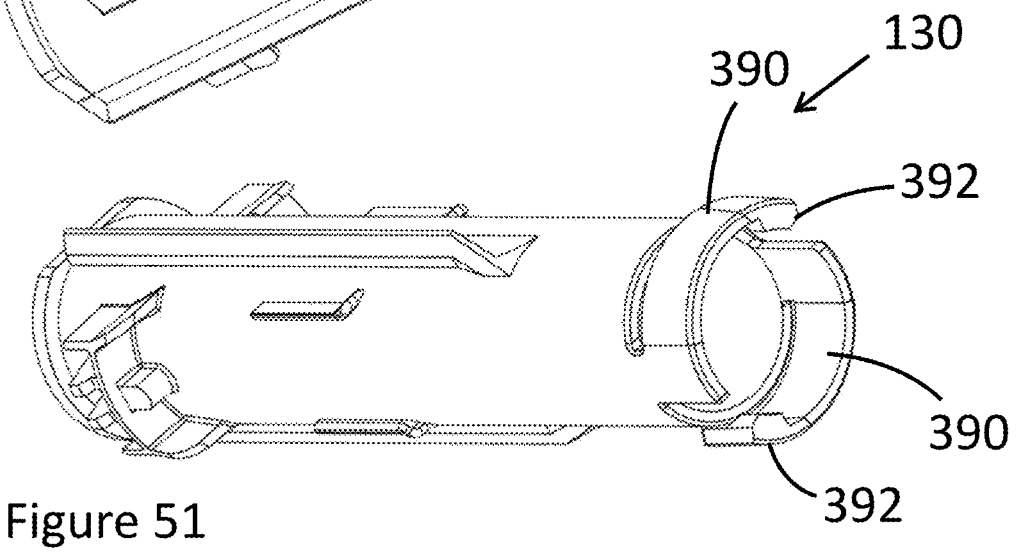
Figure 51
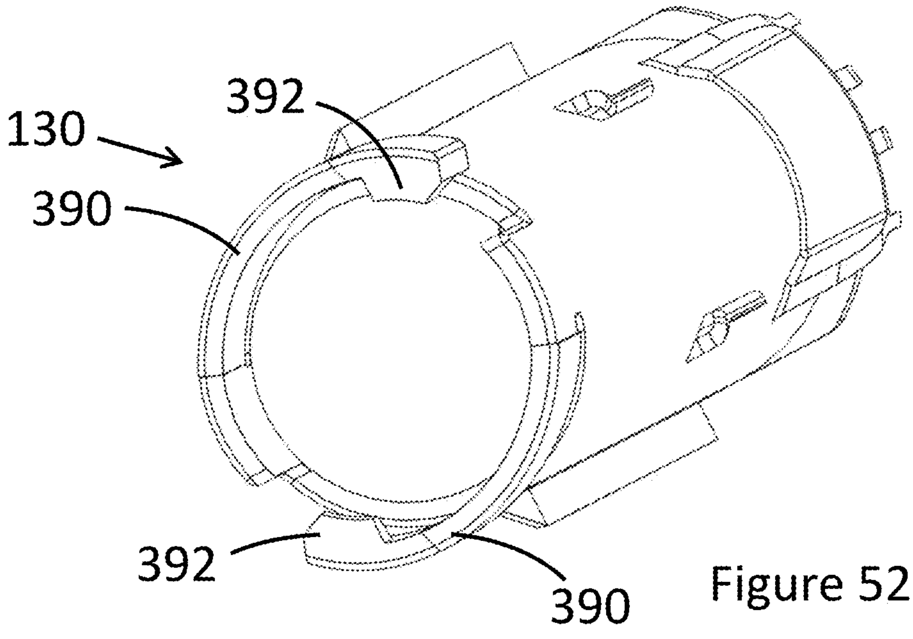
Figure 52

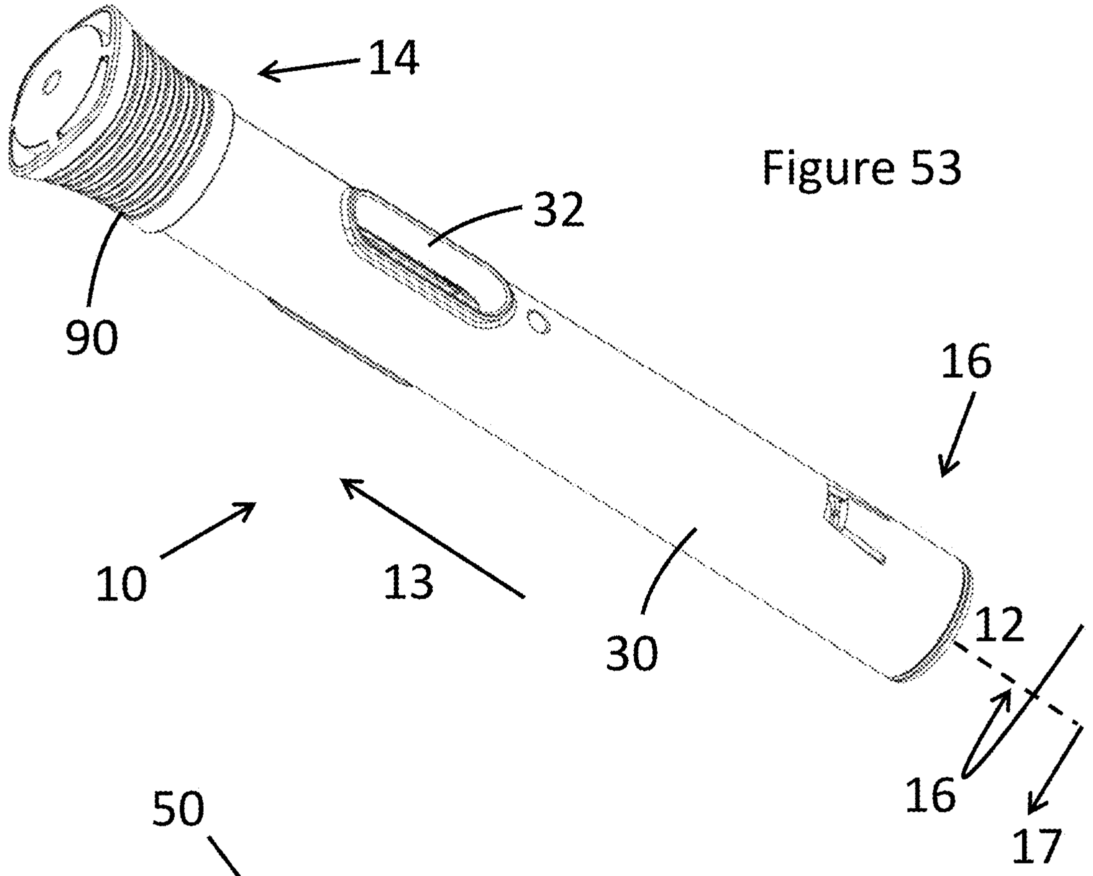
Figure 53
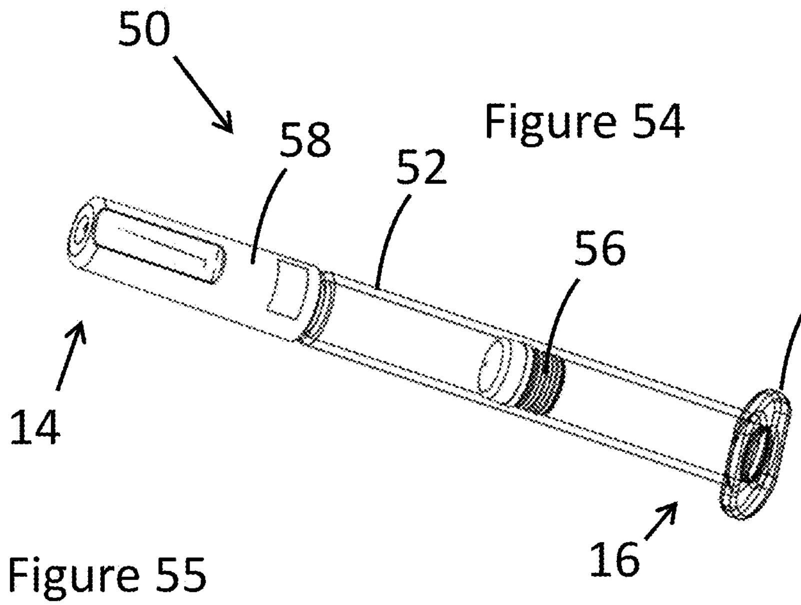
Figure 54
Figure 55
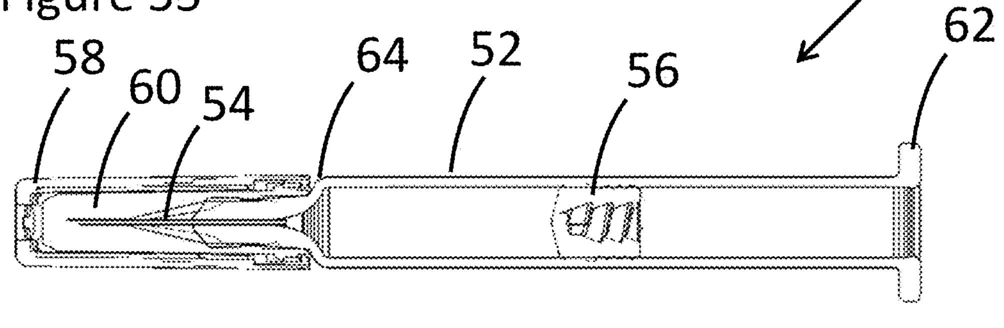

SYRINGE CARRIERS

CROSS REFERENCE TO RELATED APPLICATIONS

The present application is a U.S. National Phase Application pursuant to 35 U.S.C. § 371 of International Application No. PCT/EP2021/086939 filed Dec. 21, 2021, which claims priority to U.S. Provisional Patent Application No. 63/149,380, filed 15 Feb. 2021; U.S. Provisional Patent Application No. 63/153,408, filed 25 Feb. 2021; U.S. Provisional Patent Application No. 63/158,580, filed 9 Mar. 2021; U.S. Provisional Patent Application No. 63/162,601, filed 18 Mar. 2021; U.S. Provisional Patent Application No. 63/178,577, filed 23 Apr. 2021; and European Patent Application No. 21187327.8, filed Jul. 23, 2021. The entire disclosure contents of these applications are herewith incorporated by reference into the present application.

TECHNICAL FIELD

Syringe carriers for medicament delivery devices such as autoinjectors.

BACKGROUND

Medicament delivery devices such as autoinjectors often have a syringe carrier to support a syringe (typically a glass syringe) within the medicament delivery device. Although existing syringe carriers can be effective at supporting the syringe, the inventors have appreciated that further improvements can be made.

SUMMARY

The present disclosure concerns a number of different concepts for supporting a syringe in a medicament delivery device as described below.

The present disclosure is defined by the appended claims, to which reference should now be made.

An aspect concerns a medicament delivery device sub-assembly extending along a longitudinal axis from a proximal end to a distal end, the medicament delivery device sub-assembly comprising a tubular housing, a tubular syringe carrier inside the tubular housing and a syringe inside the syringe carrier, wherein the syringe comprises a needle shield and a medicament container comprising a shoulder, wherein the tubular housing comprises a flexible arm extending in the axial direction relative to the longitudinal axis, the flexible arm comprising an inwardly extending protrusion, wherein the inwardly extending protrusion is arranged in a gap between the shoulder and the needle shield, wherein the syringe carrier comprises a proximal portion and a distal portion, and the proximal portion is arranged adjacent to the flexible arm of the tubular housing so that movement of the flexible arm of the tubular housing in a radial direction relative to the longitudinal axis is restricted by the proximal portion of the syringe carrier.

Optionally, the syringe carrier comprises an axially flexible structure that allows the syringe carrier to shorten its length in the axial direction during assembly. Optionally, the proximal portion of the syringe carrier comprises a ring. Optionally, the axially flexible structure is attached to the distal end of the ring.

Optionally, the proximal portion of the syringe carrier comprises an arm extending in the axial direction. Optionally, the arm of the syringe carrier is inflexible. Optionally, a distal end of the arm is attached to a ring.

Optionally, the distal portion of the syringe comprises a base and an arm, and the proximal portion of the syringe is attached to the proximal end of the arm. Optionally, the base is tubular. Optionally, the needle shield comprises a rigid needle shield. Optionally, the inwardly extending protrusion is arranged in a gap between the shoulder and the rigid needle shield. Optionally, the flexible arm of the housing is attached to the rest of the housing at the distal end of the flexible arm.

An aspect concerns a medicament delivery device sub-assembly comprising: a housing extending along an axis from a proximal end to a distal end, the housing describing a tubular space within the housing, the housing comprising an arm extending into the tubular space, a syringe carrier arranged inside the tubular housing, the syringe carrier comprising an arm, and a syringe arranged inside the syringe carrier, wherein the arm of the housing comprises a first surface facing towards the distal end of the housing, and wherein a shoulder of the syringe is arranged adjacent to the first surface, wherein the arm of the housing comprises a second surface facing away from the axis, and wherein the arm of the housing is adjacent to the arm of the syringe carrier so that the arm of the housing is restricted from moving away from the axis by the arm of the syringe carrier.

Optionally, the arm of the syringe carrier extends in the proximal direction at the proximal end of the syringe carrier. Optionally, the first surface is on a protrusion of the arm of the housing. Optionally, the protrusion of the arm of the housing extends from the arm towards the axis. Optionally, the syringe carrier is tubular.

An aspect concerns a method of assembling a medicament delivery device sub-assembly as described above, the method comprising the steps of: providing the housing, the syringe carrier and the syringe; and inserting the syringe carrier and the syringe into the housing. Optionally, the step of inserting the syringe carrier and the syringe into the housing comprises, in either order, the steps of inserting the syringe carrier into the housing and inserting the syringe into the syringe carrier. Optionally, the step of inserting the syringe carrier and the syringe into the housing comprises the following steps in the following order: inserting the syringe carrier into a first position in the housing; inserting the syringe into the syringe carrier, either before or after inserting the syringe carrier into the first position in the housing; and moving the syringe carrier from the first position to a final position in the housing, wherein the final position in the housing is closer to the proximal end than the first position.

Optionally, the syringe carrier and the syringe are both inserted into a distal end of the housing. Optionally, the length of the syringe carrier varies during assembly. Optionally, the length of the syringe carrier is reduced during assembly by interaction of a proximal end of the syringe carrier with an arm of the housing. Optionally, a needle shield of the syringe pushes an arm of the housing away from the longitudinal axis during assembly. Optionally, the arm of the housing limits the proximal movement of the proximal portion of the syringe carrier whilst the arm is pushed away from the longitudinal axis.

An aspect concerns a syringe carrier for a medicament delivery device, the syringe carrier extending along a longitudinal axis from a proximal end to a distal end, the syringe carrier comprising: a plurality of arms extending in the axial direction at the proximal end of the syringe carrier, wherein the arms are spaced apart in the circumferential direction relative to the longitudinal axis around the proximal end of the syringe carrier; and a plurality of flexible strips, the plurality of flexible strips describing at least part of a ring in the circumferential direction around the longitudinal axis, wherein each one of the plurality of strips extends in the circumferential direction from a first end attached to one of the plurality of arms to a second end attached to another of the plurality of arms, wherein each of the plurality of flexible strips describes an arc, and the middle of the arc is closer to the longitudinal axis than the first end and the second end.

Optionally, the plurality of arms comprises four to six arms. Optionally, the number of flexible strips is the same as the number of arms. Optionally, the plurality of arms are inflexible. Optionally, the plurality of flexible strips are configured to flex outwards when a syringe is inserted into the syringe carrier. Optionally, the plurality of arms each extend from a proximal end to a distal end. Optionally, the distal end of each of the plurality of arms is attached to the rest of the syringe carrier. Optionally, the plurality of arms is attached to the plurality of flexible strips at the proximal end of the arms.

Optionally, the syringe carrier comprises a tubular base at the distal end. Optionally, the plurality of flexible strips are arranged to flex from the position where the middle of the arc is closer to the longitudinal axis than the first end and the second end to a position where the middle of the arc is further from the longitudinal axis than the first end and the second end to allow a needle shield of a syringe to pass between the plurality of flexible strips.

Optionally, the arms and the strips alternate in the circumferential direction.

Optionally, the plurality of flexible strips form a complete ring in the circumferential direction around the longitudinal axis. Optionally, a distal end of each of the plurality of arms is attached to a second ring. Optionally, the syringe carrier is tubular.

An aspect concerns a medicament delivery device sub-assembly comprising a housing, a syringe carrier as described above inside the housing, and a syringe inside the syringe carrier. Optionally, at least part of each of the plurality of flexible strips is in a gap between a needle shield of the syringe and a shoulder of the syringe. Optionally, a portion of the housing restricts movement away from the longitudinal axis by the plurality of flexible strips.

An aspect concerns a syringe carrier for a medicament delivery device, wherein the syringe carrier comprises an expandable ring. The expandable ring comprises one or more hinges spaced around the circumference of the expandable ring. The ring comprises two or more hinges, and wherein the hinges are convexly curved strips.

An aspect concerns a method of assembling a medicament delivery device sub-assembly comprising a syringe carrier as described above or a medicament delivery device sub-assembly as described above, the method comprising the steps of: providing a housing, the syringe carrier and a syringe; and inserting the syringe carrier and the syringe into the housing. Optionally, the step of inserting the syringe carrier and the syringe into the housing comprises, in either order, the steps of inserting the syringe carrier into the housing and inserting the syringe into the syringe carrier Optionally, the step of inserting the syringe carrier and the syringe into the housing comprises the following steps in the following order: inserting the syringe carrier into a first position in the housing; inserting the syringe into the syringe carrier, either before or after inserting the syringe carrier into the first position in the housing; and moving the syringe carrier from the first position to a final position in the housing, wherein the final position in the housing is closer to the proximal end than the first position.

Optionally, during the method of assembling the medicament delivery device sub-assembly, at least part of each of the plurality of protrusions is inserted into a gap between a needle shield of the syringe and a shoulder of the syringe.

An aspect concerns a syringe carrier for a medicament delivery device, wherein the syringe carrier extends along a longitudinal axis, wherein the syringe carrier comprises a plurality of protrusions extending in the axial direction relative to the longitudinal axis from a proximal end of the syringe carrier, the plurality of protrusions each extending from a proximal end to a distal end, wherein the distal end of each of the plurality of protrusions is attached to the rest of the syringe carrier by a hinge and wherein each of the plurality of protrusions is pivotable about the hinge so that the plurality of protrusions can move from a first position to a second position, wherein in the second position, the proximal end of each of the plurality of protrusions is closer to the longitudinal axis than the distal end of each of the plurality of protrusions, so that the plurality of protrusions can support a syringe inside the syringe carrier, and wherein the proximal ends of the plurality of protrusions are further from the longitudinal axis in the first position than in the second position.

Optionally, the first position is a relaxed position and the second position is a biased position. Optionally, the plurality of protrusions are equally spaced around the circumference. Optionally, each of the plurality of protrusions does not comprise a radially inwardly extending protrusion extending from the protrusion. Optionally, the thickness of the material of the hinge is narrower in the radial direction than the thickness of the material of the plurality of protrusions. Optionally, the distal end of each of the plurality of protrusions is attached by the hinge to a ring of the syringe carrier. Optionally, the ring is attached to a base by at least one arm.

Optionally, the thickness of the material of the hinge is narrower in the radial direction than the thickness in the radial direction of the material of the plurality of protrusions and the thickness in the radial direction of the material of the ring. Optionally, the plurality of protrusions comprises at least 9 protrusions, and preferably comprises between 10 and 14 protrusions. Optionally, the protrusions are flexible. Optionally, the proximal end of each of the plurality of protrusions is tapered.

An aspect concerns a medicament delivery device sub-assembly comprising a housing, a syringe carrier as described above inside the housing, and a syringe inside the syringe carrier, wherein at least part of each of the plurality of protrusions is in a gap between a needle shield of the syringe and a shoulder of the syringe.

Optionally, at least half of the length of each of the plurality of protrusions is in a gap between a needle shield of the syringe and a shoulder of the syringe. Optionally, a portion of the housing restricts movement away from the longitudinal axis by the plurality of protrusions. Optionally, the portion of the housing is a ring of an inner portion of the housing.

An aspect concerns a method of assembling a medicament delivery device sub-assembly comprising a syringe carrier as described above or a medicament delivery device sub-assembly as described above, the method comprising the steps of: providing a housing, the syringe carrier and a syringe; and inserting the syringe carrier and the syringe into the housing. Optionally, the step of inserting the syringe carrier and the syringe into the housing comprises, in either order, the steps of inserting the syringe carrier into the housing and inserting the syringe into the syringe carrier.

Optionally, the step of inserting the syringe carrier and the syringe into the housing comprises the following steps in the following order: inserting the syringe carrier into a first position in the housing; inserting the syringe into the syringe carrier, either before or after inserting the syringe carrier into the first position in the housing; and moving the syringe carrier from the first position to a final position in the housing, wherein the final position in the housing is closer to the proximal end than the first position. Optionally, when the syringe carrier is moved to the final position in the housing, the plurality of protrusions are pushed towards the longitudinal axis to support a shoulder of the syringe.

An aspect concerns a medicament delivery device comprising a syringe carrier as described above, or a medicament delivery device sub-assembly as described above. Optionally, the medicament delivery device is an autoinjector.

An aspect concerns a method of assembling a medicament delivery device, comprising the method of assembling a medicament delivery device sub-assembly as described above. Optionally, the method of assembling a medicament delivery device is a method of assembling an autoinjector.

Where a needle shield is mentioned above, the needle shield may be a rigid needle shield.

BRIEF DESCRIPTION OF THE DRAWINGS

Embodiments of the present disclosure will now be described by way of example only and with reference to the accompanying drawings as listed below.

FIGS. 7, 8, 9, 10, 11 and 12 show partial cross-section views during assembly of an autoinjector comprising the syringe carrier of FIG. 5 and the housing of FIG. 1.

FIGS. 19, 20 and 21 show different perspective views of a syringe carrier that could be used in the medicament delivery device of FIG. 14.

FIG. 31 shows a side view of a syringe carrier.

FIGS. 32 and 33 show cross-section views of part of a syringe carrier and part of a syringe carrier cover.

FIGS. 34 and 35 show cross-section views of part of a syringe carrier and part of a syringe carrier cover.

FIGS. 42 and 43 show different perspective views of a syringe carrier.

FIGS. 46 and 47 show different perspective views of a syringe carrier.

FIG. 48 shows a perspective cross-section view of part of the syringe carrier of FIG. 46.

FIG. 49 shows a cross-section view of part of a medicament delivery device comprising the syringe carrier of FIG. 46.

FIGS. 50, 51 and 52 show different perspective views of a syringe carrier.

FIG. 53 shows a perspective view of an example autoinjector.

FIG. 54 shows a perspective view of an example syringe.

FIG. 55 shows a cross-section view of the example syringe of FIG. 54.

DETAILED DESCRIPTION

In general, the present disclosure describes various syringe carriers for medicament delivery devices such as autoinjectors. Generally, these syringe carriers are for use in devices in which the syringe is inserted into the device (for example into a housing of the device) in the axial direction during assembly.

The 1 ml tall syringe is by far the most used primary container within the autoinjector market. The syringe usually is made out of glass; a material less suited for impact loads. The 1 ml tall syringe can be fitted with a flexible needle shield only or with an additional rigid needle shield. The latter protects the user from needle stick injuries when administered as a prefilled syringe only, but creates a problem when assembled into an auto injector. When the diameter of the RNS as large as the barrel diameter of the 1 ml tall syringe, this limits the possibility of supporting the syringe at its neck or shoulder. Supporting the syringe by the finger flange is a risky way to go since the flange is more sensitive to breakage due to its geometrical shape.

This problem is usually solved by having a c-shaped support that is allowed to bend during syringe assembly or by flexing supports that are later supported by the auto injector enclosure. However, splitting the syringe carrier means the parts can tangle during bulk component transport. In addition, a c-shaped carrier can transmit large forces to the RNS, which can cause it to move during assembly and affect sterility.

Considering the potential problems with the existing designs, the applicant has appreciated that an alternative approach could provide a more satisfactory solution.

Figure 1:
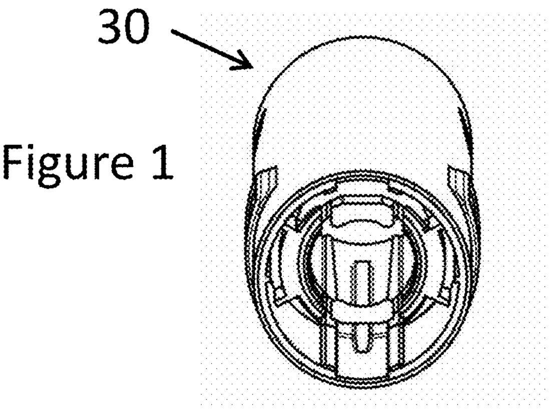
FIGS. 1, 2, 3 and 4 show various views of a housing for a medicament delivery device.
Figure 2:
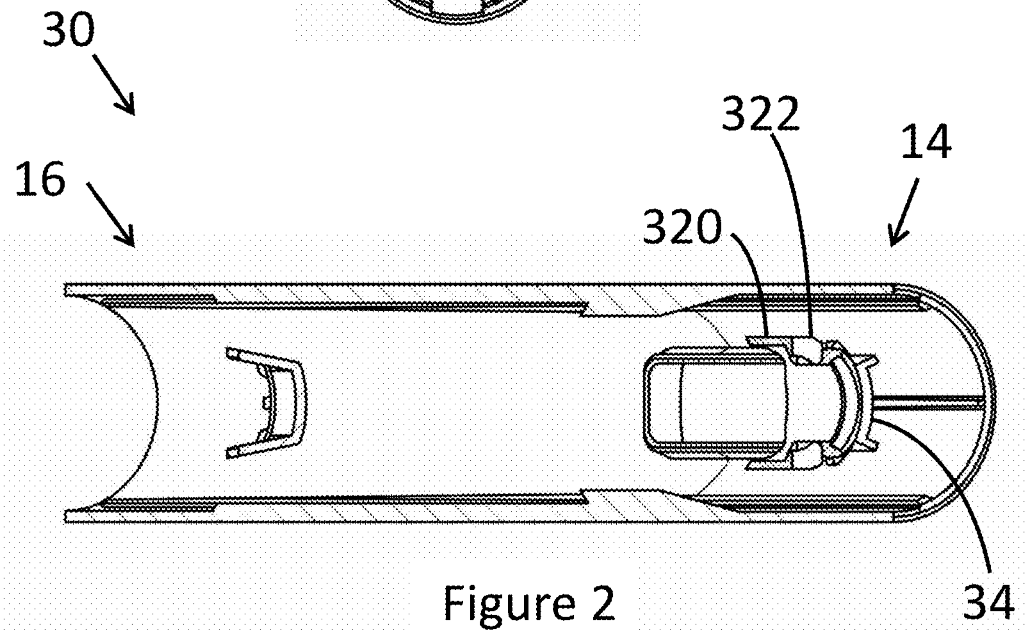

A medicament delivery device body (housing) 30 is provided with flexible arms 320 configured to hold the syringe at its shoulder, as shown in FIGS. 1 and 2. The arms 320 extend in the axial direction from a proximal end to a distal end. In this example, the distal end of the arms is attached to the housing (specifically to an inner part 34 of the housing 30 in this particular example, though this particular housing shape can be altered—for example, the arm could alternatively be attached to a different part of the housing), and a protrusion 322 extends from the proximal end of the arm. Alternatively, the proximal end of the arms is attached to the housing and the protrusion 322 extends from the distal end of the arm. Instead of extending from an end of the arm, the protrusion could also be spaced apart in the axial direction from the end of the arm. The protrusion 322 extends in the radial direction from the arm, and specifically the protrusion 322 extends towards the axis (so radially inwardly) from the arm, making it an inwardly extending protrusion. The specific shape of the protrusion could be varied, for example depending on the shape of the syringe (for example depending on the shape of the gap between the RNS and the shoulder of the syringe). The closest distance between the protrusions is less than the diameter of the RNS.

Figure 3:
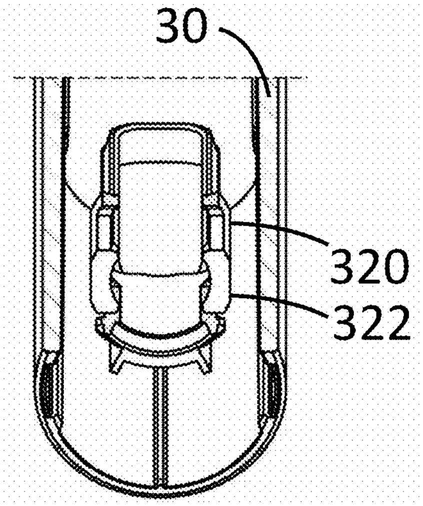
Figure 4:
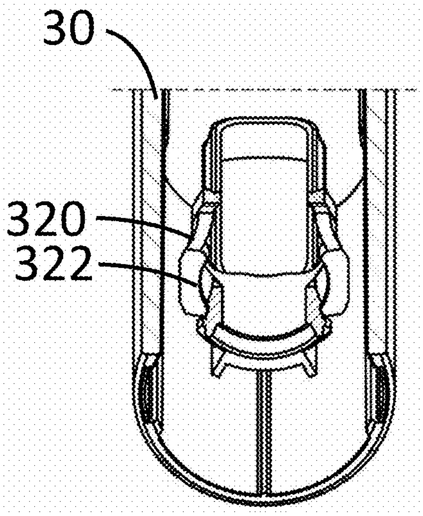

The two flexible arms 320 can displace radially as the syringe is inserted (so that the arms can pass the RNS of the syringe); the relaxed and flexed states are shown in FIGS. 3 and 4 respectively.

Figure 5:
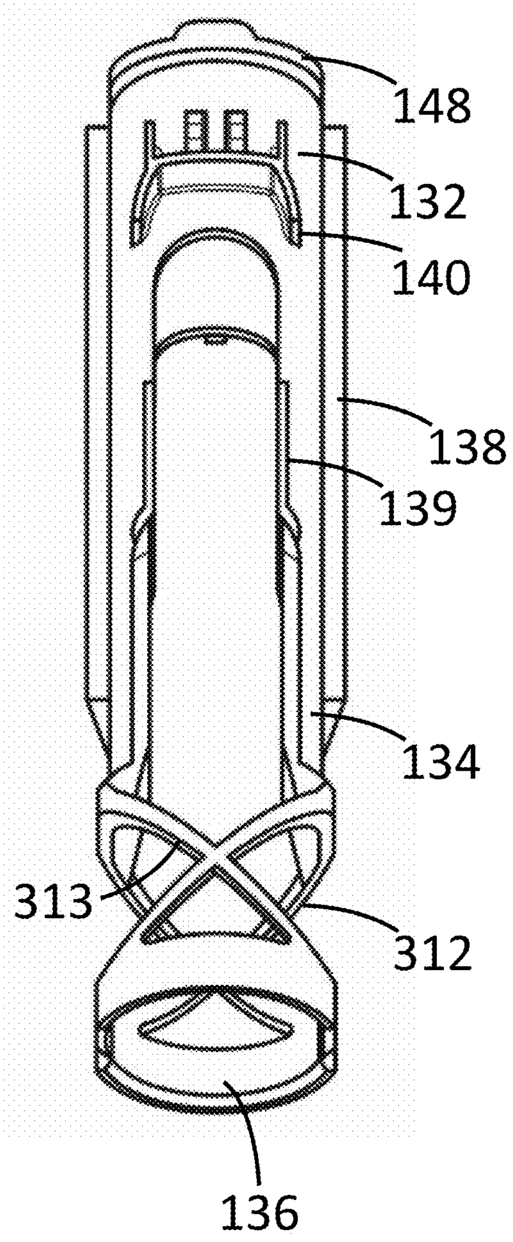
FIGS. 5 and 6 show perspective views of a syringe carrier to be used with the housing of FIG. 1.
Figure 6:
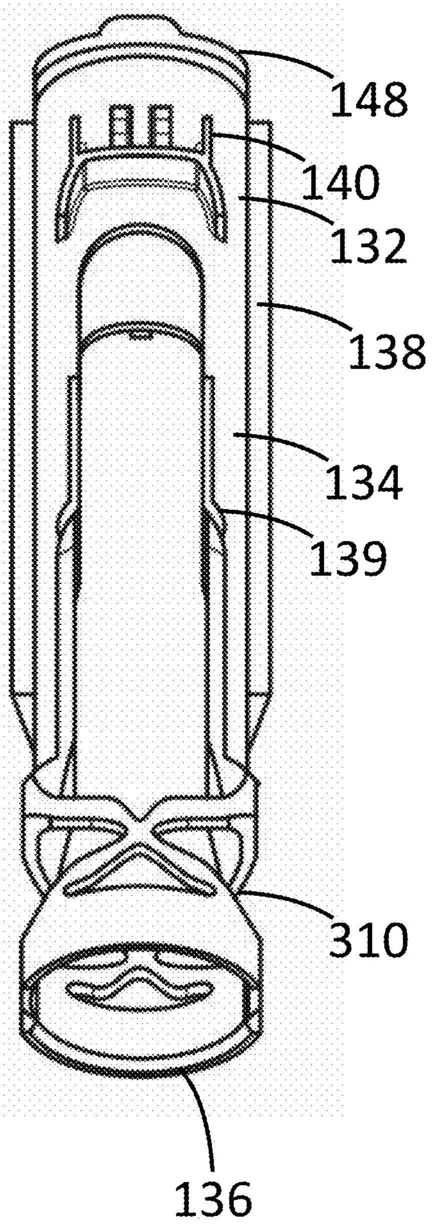

To prevent the arms from flexing when the syringe is in place, a syringe carrier 130 with a ring (locking ring) 136 is used. The locking ring can be considered to be a proximal portion of the syringe carrier. The locking ring is connected to the rest of the syringe carrier via an axially flexible structure 310 allowing the syringe carrier to shorten its length during assembly. The syringe carrier 130 is shown in FIGS. 5 and 6, with FIG. 5 showing a default (or relaxed) state and FIG. 6 showing a compressed state.

In this particular example, the axially flexible structure 310 is a pair of arms, namely a first arm 312 of the axially flexible structure and a second arm 313 of the axially flexible structure. The first arm 312 and the second arm 313 are each an X-shaped arm; that is, they are each made up of four arms that are joined together at one end of each of the four arms. The other end of two of the arms is attached to the ring 136. The other end of the other two arms are attached to the arms 134 of the syringe carrier (in this case one to each arm 134, though they could both be attached to the same arm). As a result, the arms 312, 313 can be considered to be joining together the proximal portion (the ring) and the distal portion (the arms 134 and the base 132) of the syringe carrier. More generally, though, many different axially flexible structures could be provided instead of this particular structure, including concertina shapes, hinges, helical shapes or the like. In general, it is important that the axially flexible structure can elastically reduce in length when the syringe carrier is compressed in the axial direction.

Figure 7:
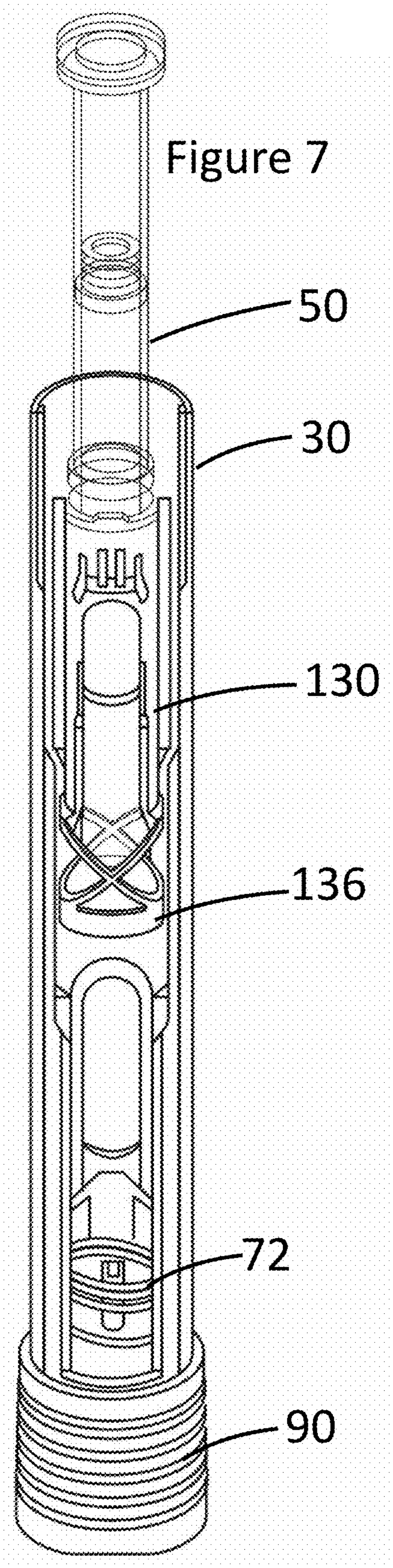
Figure 8:
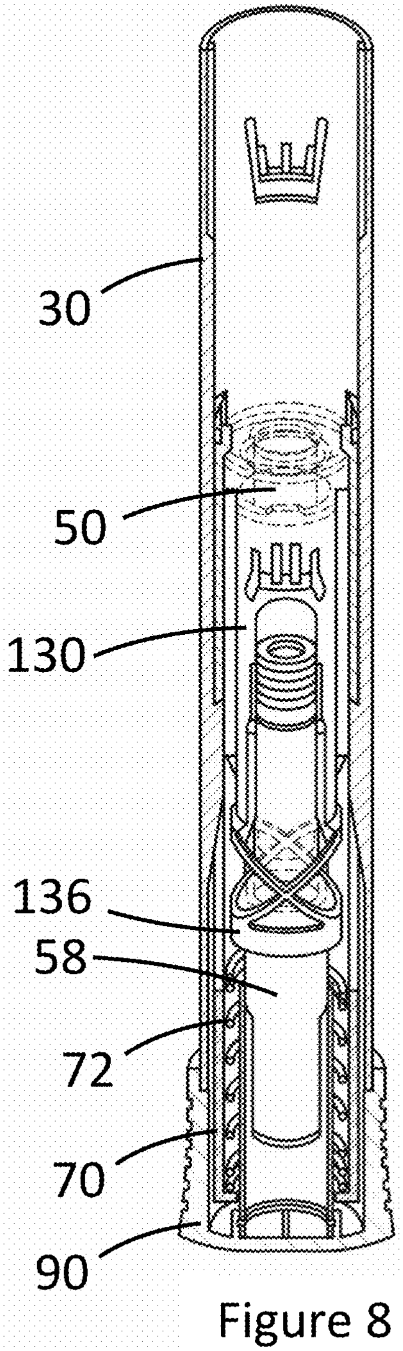

As the device is assembled a syringe is first placed inside the syringe carrier (optionally, the syringe carrier is already inside the housing at this point, as shown in FIG. 7), resulting in the syringe carrier being in a first position relative to the housing. The syringe carrier and the syringe are then moved axially towards the front (proximal end) of the device (i.e. in the proximal direction relative to the housing). FIG. 7 shows the syringe being inserted into the syringe carrier, and FIG. 8 shows the syringe and syringe carrier during insertion (as the syringe carrier and the syringe move axially towards the front).

The diameter of the RNS 58 forces the two flexible arms 320 of the housing to radially flex outwards as the syringe is pressed through the housing and past the flexible arms. The radial flex of the arms of the housing prevents the locking ring 136 from entering its final position, as seen in FIG. 9—the arms are now in the way of the syringe carrier, stopping it from continuing to move in the proximal direction relative to the housing 30. As the syringe is subsequently pushed further in the proximal direction, the syringe carrier is compressed as shown in FIGS. 10 and 11.

Figure 12:
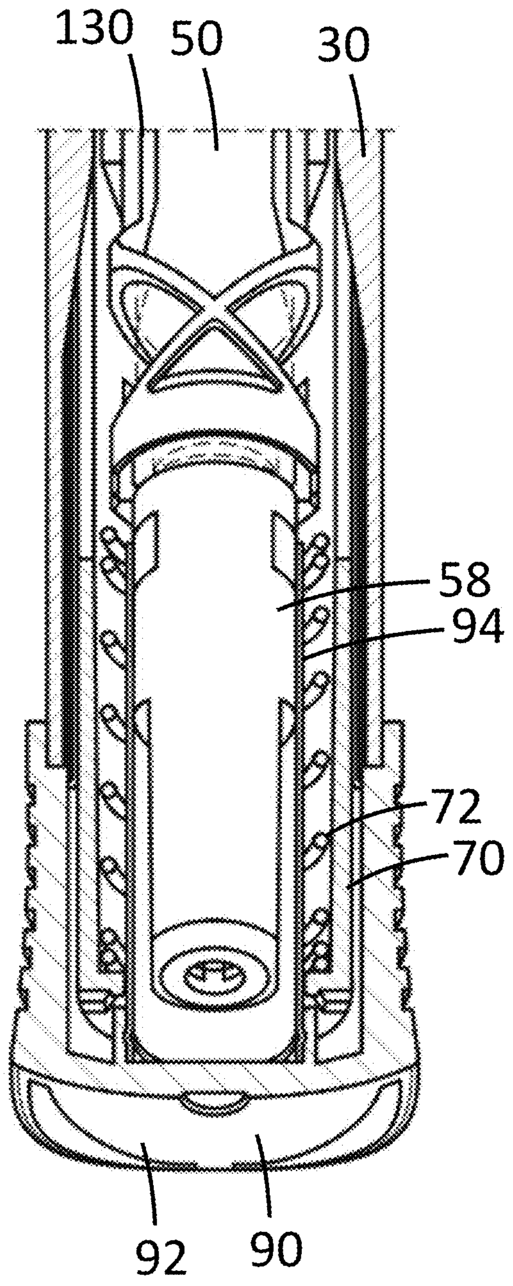

When the syringe reaches its final position the flexing arms on the housing are no longer supported (pushed outwards) by the RNS and flex back to their original positions—entering the space between the RNS and the shoulder of the syringe. The support for the compression of the compressed syringe carrier (i.e. the block on the ring 136 moving forward due to the outwardly flexed arms 320) is now removed and the locking ring moves forward and locks the flexing arms from further movement (i.e. the arms are now restricted from moving away from the axis in the radial direction as the ring is in the way), as shown in FIG. 12. FIG. 12 shows the final position of the syringe housing relative to the housing.

Figure 13:
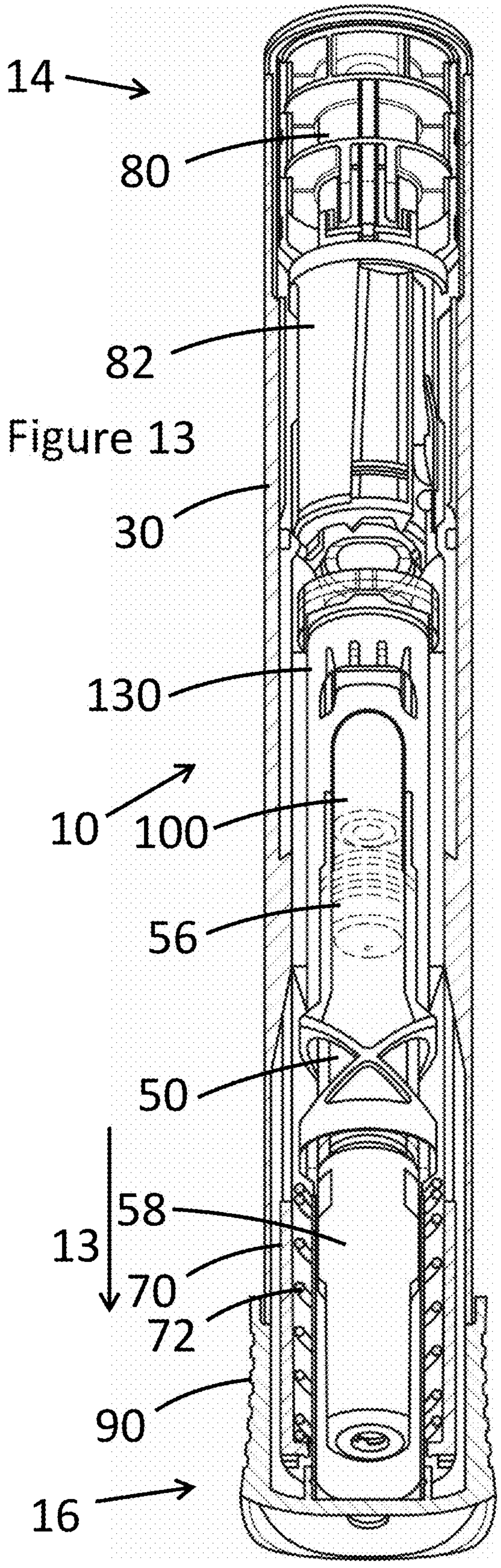
FIG. 13 shows a partial cross-section view of an autoinjector comprising the syringe carrier of FIG. 5 and the housing of FIG. 1.

The syringe insertion process is now complete and the power pack can be inserted into the housing, resulting in an autoinjector (or a medicament delivery device more generally) as shown in FIG. 13.

Figure 14:
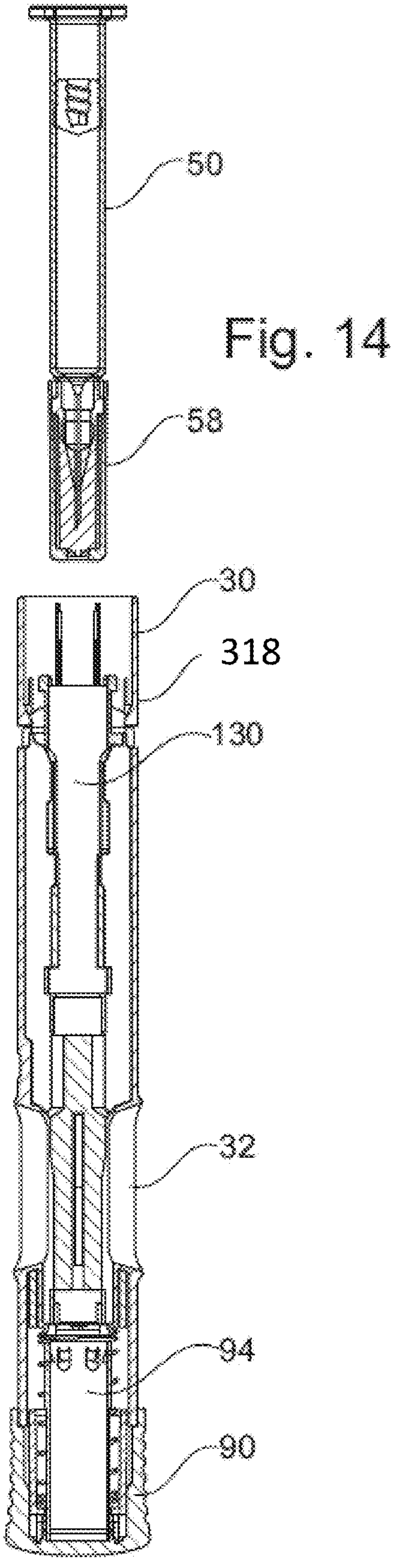
FIGS. 14 and 15 show cross-section views of a medicament delivery device at different stages of assembly.
Figure 15:
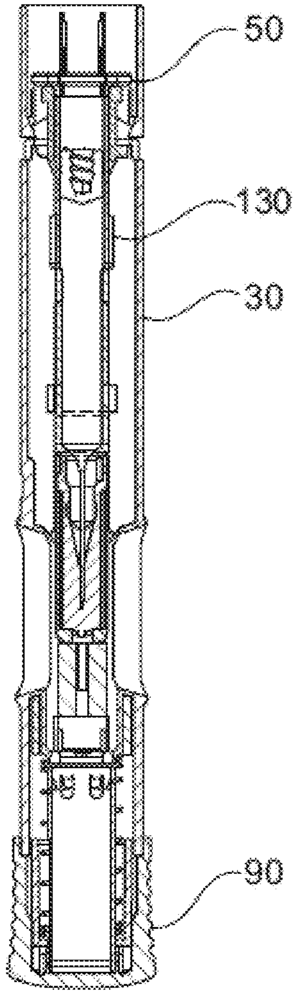
Figure 16:
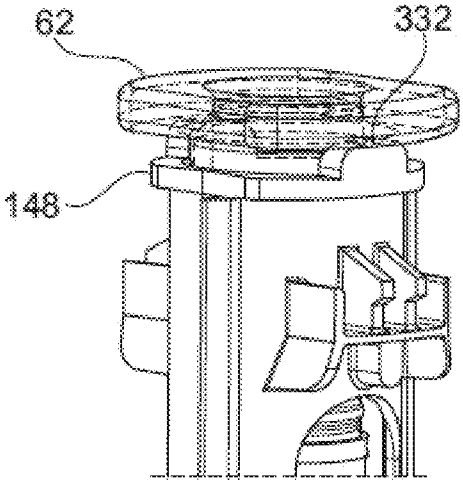
FIG. 16 shows a perspective view of a syringe and a syringe housing of the medicament delivery device of FIG. 14.

Another alternative example is described with reference to FIGS. 14 to 21. In this example, a syringe carrier is first inserted into a housing in the proximal direction relative to the housing, but the syringe carrier is not pushed all the way into the housing in the proximal direction—the syringe carrier is left in a position where the syringe carrier can still move further in the proximal direction relative to the housing. This position is shown in FIG. 14. Variously shaped features such as arms, recesses, cut-outs and protrusions could be provided on the housing to engage the syringe carrier in this position, but in this case proximally extending flexible arms 318 of the housing 30 are provided, with the distal end of the arms attached to the housing and the proximal end of the arms free to move radially relative to the housing, and with radially inwardly extending protrusions on the proximal end of the arms to engage the arms of the syringe carrier. Optionally, the point at which the syringe carrier is released can be controlled by restricting movement of the arms 318 (and hence the protrusions) away from the axis during assembly, thereby fixing the position of the housing relative to the syringe carrier. When this restriction is subsequently removed, the syringe carrier can then be disengaged from the protrusions, thereby allowing the syringe carrier to move relative to the housing.

A syringe is then inserted into the housing and into the syringe carrier (though the syringe could be inserted into the syringe carrier before the syringe carrier is even inserted into the housing). This results in the position shown in FIG. 15, where the syringe carrier is in a first position. As shown in more detail in FIG. 16, at this point the flange 62 of the syringe 50 abuts the distal end of the syringe carrier 130 in this example (in this case, the flange 62 of the syringe 50 abuts an optional distally extending protrusion 332 that extends from an optional distal flange 148 of the syringe carrier, though the distal end of the syringe carrier could also be a different shape).

Figure 17:
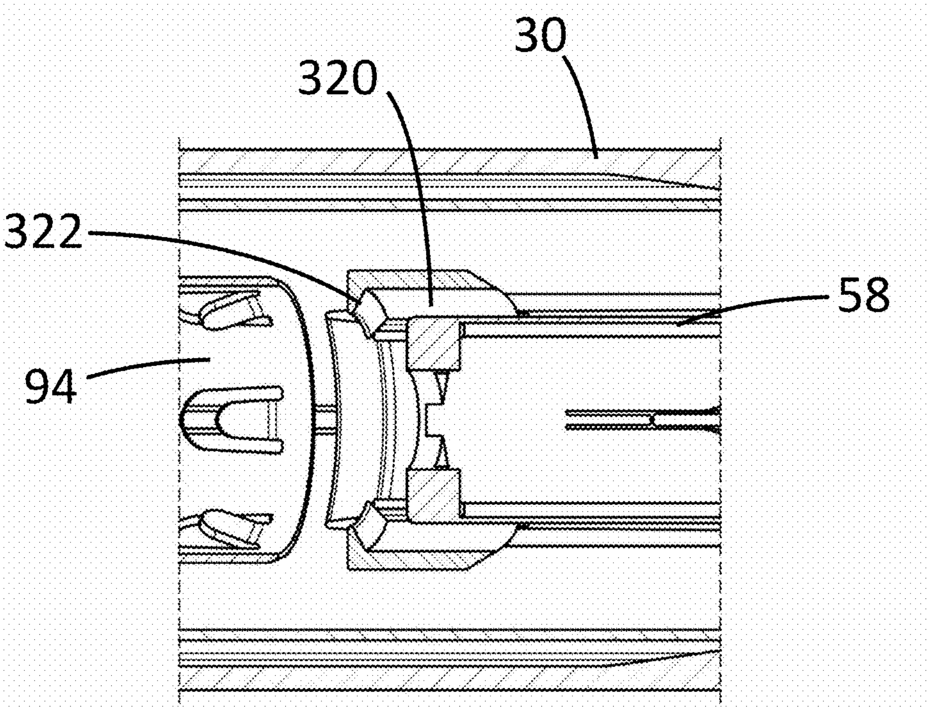
FIG. 17 shows another cross-section view of the medicament delivery device of FIG. 14 during assembly.

Continued pushing of the syringe 50 in the proximal direction relative to the housing 30 results in the RNS 58 of the syringe pushing two arms 320 of the housing apart. FIG. 17 shows the relative position of the arms 320 and the RNS 58. The housing 30 has a similar structure to the housing shown in FIGS. 1 to 4 (and indeed the two housings are interchangeable). Each arm 320 has a protrusion 322 on the proximal end, and the protrusion ends up in the gap between the RNS 58 and the shoulder 64 of the syringe.

The syringe holder is then pushed in the proximal direction relative to the housing and the syringe. As a result, the proximal end of the syringe carrier (two proximally facing arms in this example, as can be seen from FIGS. 19 to 21, which show three views of the syringe carrier) is moved to a position where it blocks the arms of the housing from moving away from the axis, thereby stopping the protrusions of the arms from moving out of the gap between the RNS and the syringe shoulder, thereby keeping the protrusions in a position in which they support the syringe. This final position can be seen in FIG. 18.

Figure 18:
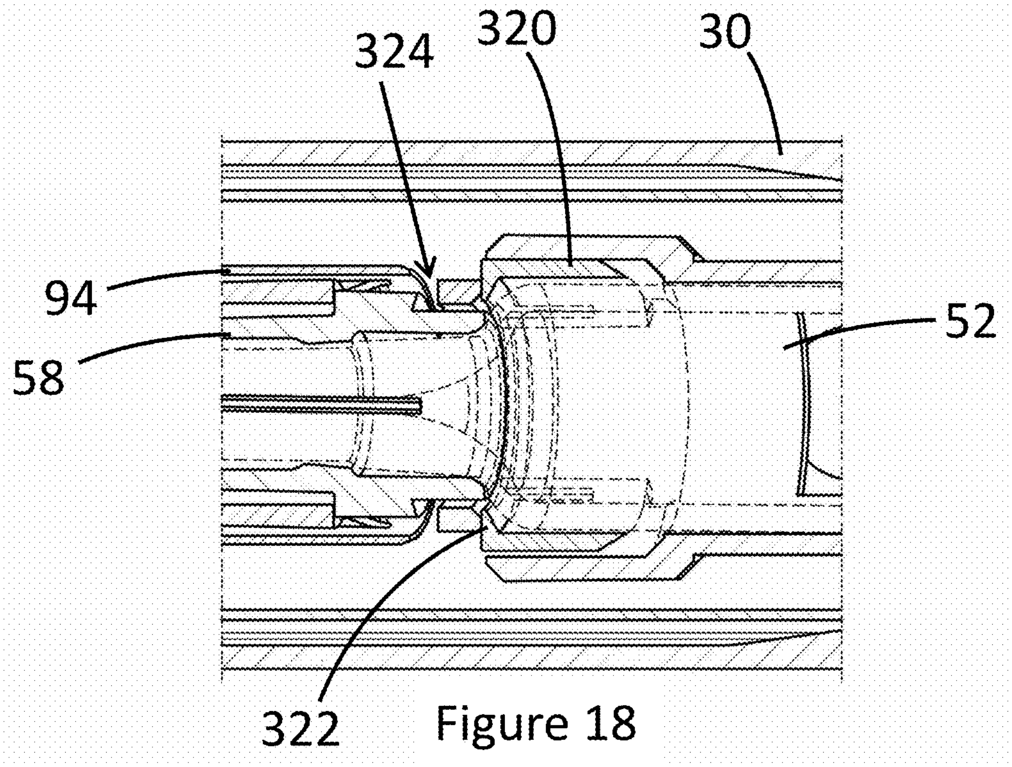
FIG. 18 shows a cross-section view of the medicament delivery device of FIG. 14 after assembly has been completed.

Depending on the shape of the gap and the shape and flexibility of the arms 320 and the protrusions 322, these assembly steps may be sufficient on their own, as the protrusions can enter the gap at a proximal end of the gap (reference numeral 324 in FIG. 18), with the syringe then moving slightly further in the proximal direction relative to the housing to arrive in the position shown in FIG. 18.

If the gap is smaller, making the above approach impractical, the assembly approach could be adjusted accordingly (and the syringe carrier dimensions and/or shape might also need slight adjustments). For example, the syringe carrier could be rotated into place after the syringe has reached its final position, or the syringe carrier could be moved in the proximal direction relative to the syringe after the syringe is in its final position (the flange 62 of the syringe would then end up spaced apart in the axial direction from the protrusions 332). In both cases, the arms 360 of the syringe carrier only restrict the arms 320 of the housing after the syringe is in its final position.

FIGS. 19 to 21 show three different views of the syringe carrier 130. The syringe carrier is similar in shape to other syringe carriers described herein, comprising in particular a base 132 at the distal end of the syringe carrier and two arms 134 extending in the proximal direction from the base 132. As mentioned above, at the distal end the syringe carrier also comprises a distal flange 148 at the distal end of the base 132 and a distally extending protrusion 332 extending from the distal flange 148. At the proximal end of the arms 134, a ring 136 is attached. Two proximal arms 360 extend in the proximal direction from the ring 136. The ring 136 is optional (without the ring, the arms 360 would simply be the proximal end of the arms 134), but may help provide structural strength, and may also help reduce issues with tangling of syringe carriers (e.g. when transported in bulk). In this example, the arms 360 are further from the central axis than the ring 136 and the arms 134, though this is optional and could be altered depending on the particular shape of the syringe and other medicament delivery device components, for example.

Another syringe carrier example is shown in FIGS. 22 to 26. In this example, much of the syringe carrier is similar to those described elsewhere herein and the description will not be repeated. The proximal end of the syringe carrier comprises a plurality of proximally extending arms 340 (four in this case, although more or fewer could alternatively be provided), with flexible curved strips 342 (or hinges) extending between the arms. The strips curve convexly when unbiased (see FIG. 25), but can switch to a concave shape when pushed outwards by the RNS during assembly (see FIG. 26), allowing the RNS to pass. After the RNS has passed the curved strips, the curved strips can then unbias (relax) back to the position shown in FIG. 24. The strips can thereby support the syringe at its shoulder.

Optionally, in the final assembled position, the strips or peripheral structures are supported by one or more other components so that the flexible structure cannot deform again. For example, a protrusion on the housing of a medicament delivery device (such as the housing shown in FIG. 53) could comprise a protrusion that restricts the radial movement of one of the strips so that the strip cannot attain the position shown in FIG. 26 after device assembly.

Figure 22:
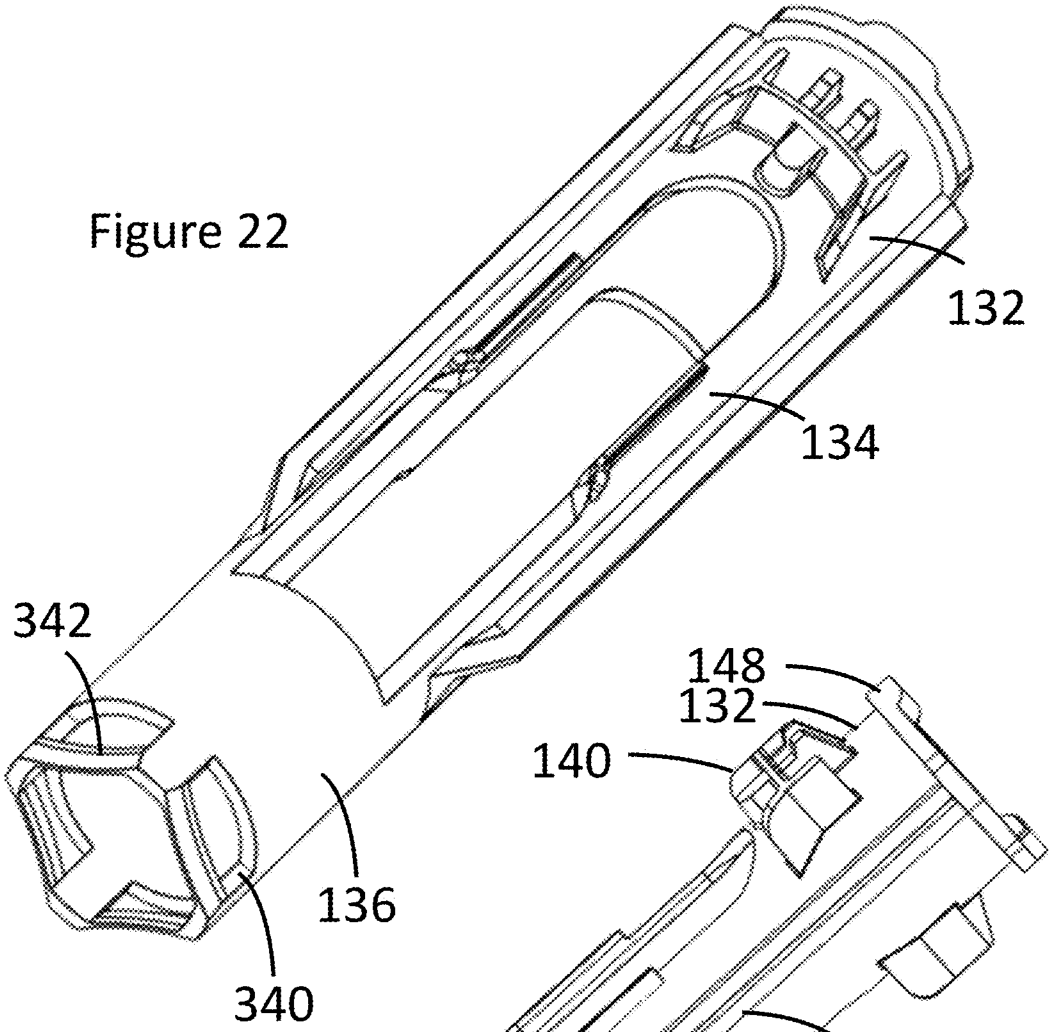
FIGS. 22 and 23 show different perspective views of a syringe carrier.
Figure 23:
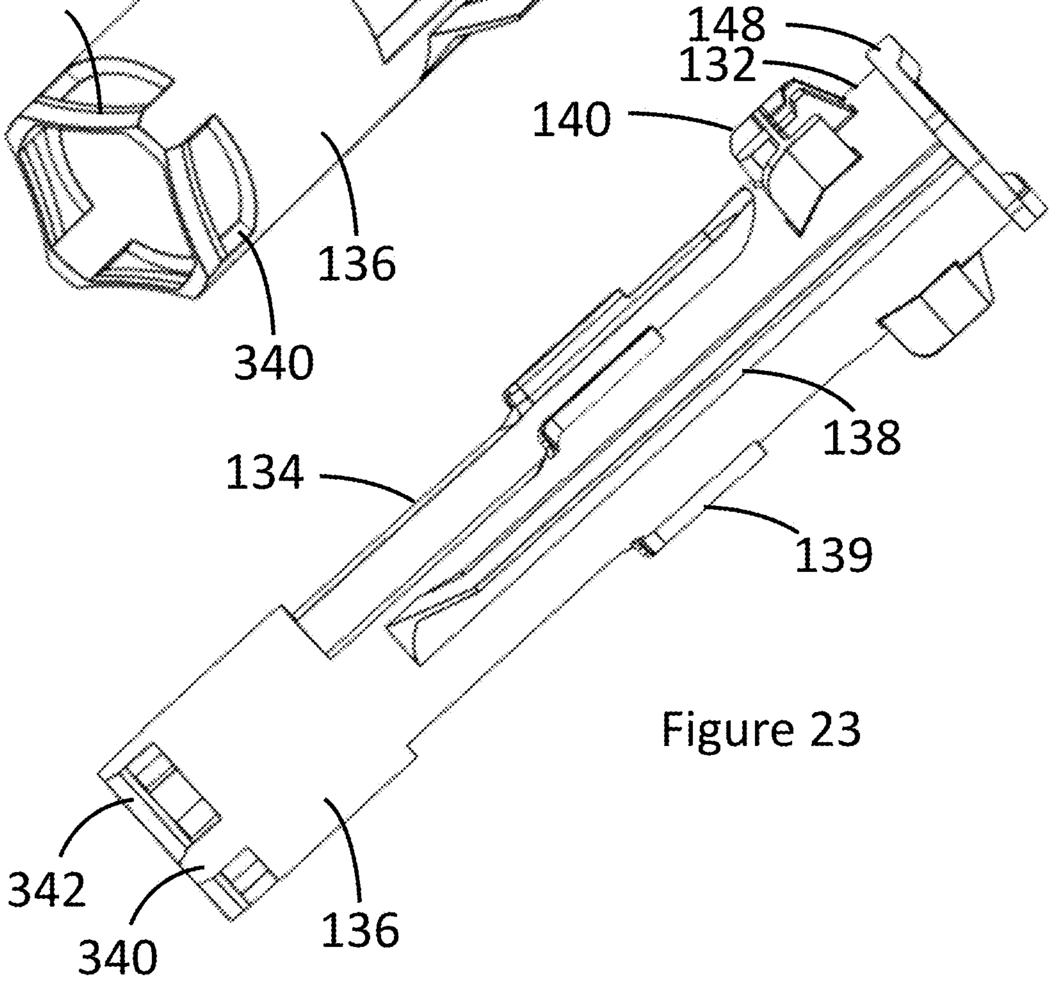
Figure 24:
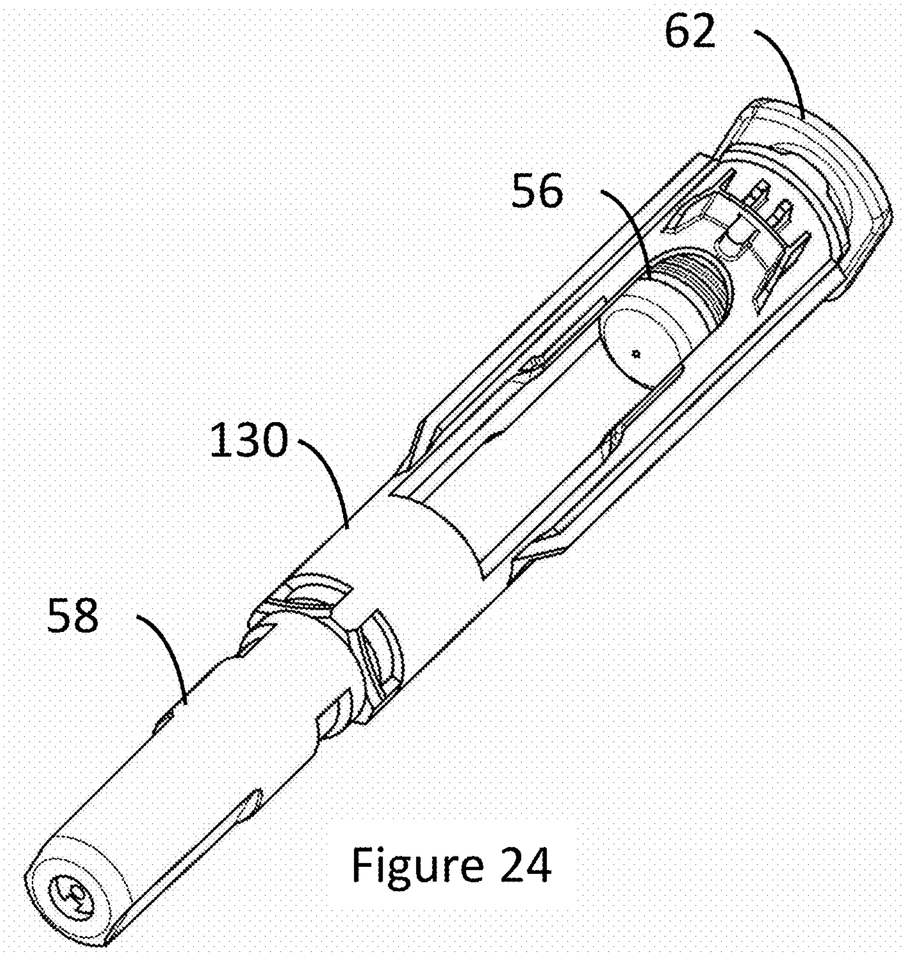
FIG. 24 shows a perspective view of the syringe carrier of FIG. 22 with a syringe inside.

FIGS. 22 and 23 show two views of a syringe carrier 130. In addition to the base 132 and arms 134, an optional ring 136 is attached to the arms 134 at its distal end and the proximally extending arms at its proximal end. The ring is not expandable. The ring can help maintain the rigidity and/or structural integrity of the syringe carrier. The ring can help reduce syringe carrier tangling during bulk transport of syringe carriers. FIG. 24 shows the syringe carrier 130 with a syringe 50 inside the syringe carrier 130.

Figure 25:
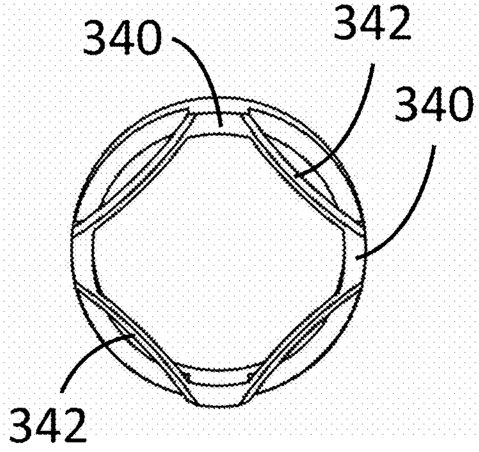
FIGS. 25 and 26 show end views of the syringe carrier of FIG. 22 in unbiased and biased states respectively.
Figure 26:
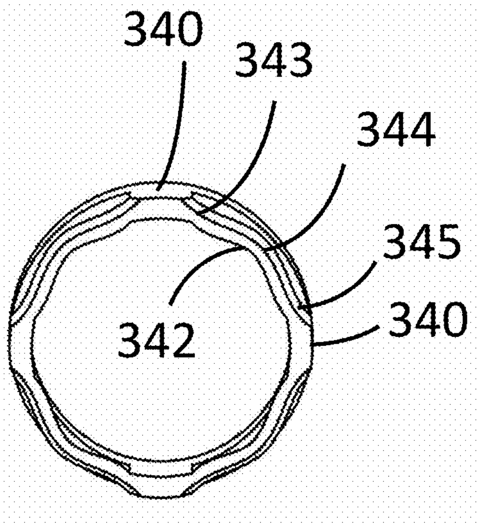

FIG. 25 shows the structure at the proximal end of the syringe carrier. In particular, four arms 340 can be seen, along with four strips 342. The four arms are spread out evenly around the circumference of the syringe carrier. A strip extends between each adjacent pair of arms (adjacent in the circumferential direction). Each one of the strips extends in the circumferential direction from a first end to a second end. For each strip, the first end is attached to one arm and the second end is attached to another arm. Each strip describes an arc. The middle of the arc is closer to the longitudinal axis than the first end and the second end. The result in this particular example is that exactly one strip extends between every adjacent pair of arms (resulting in four arms alternating with four strips when moving around the circumference of the syringe carrier). The strips are arranged to flex from the position where the middle of the arc is closer to the longitudinal axis than the first end and the second end (FIG. 25) to a position where the middle 344 of the arc is further from the longitudinal axis than the first end 343 and the second end 345 to allow a needle shield of a syringe to pass the strips (FIG. 26).

Various alternatives are also possible, for example with fewer or more arms and fewer or more strips. Two or more arms could be provided, or three or more arms, or four or more arms. Two or more strips could be provided, or three or more strips, or four or more strips. Four to six arms are preferably provided, along with the same number of strips. In the example above, the number of arms and the number of strips are the same, but there could be a different number, for example more arms than strips. For example, four arms could be provided, with only two strips, or six arms with three strips. The arms could be irregularly spaced around the circumference of the syringe carrier rather than regularly spaced. The particular shape of the arms and the strips could be varied, for example to account for differences in structure in different medicament delivery devices and with different syringes. In combination, the strips will form a partial or complete ring around the circumference of the syringe carrier—a complete ring is shown in the example in the Figures. The arms could be flexible or rigid (inflexible), but it may be beneficial for the arms to be rigid. When flexible arms are provided, the arms could be restricted from moving away from the longitudinal axis (for example by the housing) in an assembled medicament delivery device.

Figure 27:
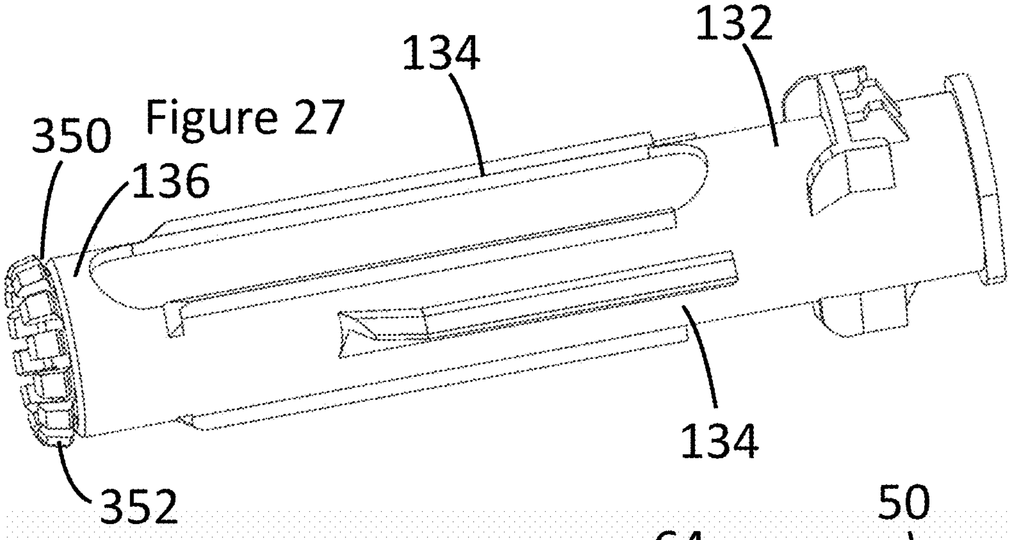
FIG. 27 shows a perspective view of a syringe carrier.

In this example, a plurality of flexible protrusions (arms) 352 extend in the proximal direction from the proximal end of the syringe carrier 130, as shown in FIG. 27. In this example, much of the rest of the syringe carrier is similar to those described elsewhere herein and the description will not be repeated. The syringe carrier comprises a base 132 and two arms 134, with the distal end of the arms attached to the base and the proximal end of the arms attached to the distal end of a ring 136. The protrusions 352 are attached to the proximal end of the ring 136. Each protrusion 352 is attached to the ring 136 by a hinge 350. As a result, the protrusions are pivotable about the hinge 350 (i.e. relative to the rest of the syringe carrier). Protrusions arranged in this way can provide a simple solution and can provide a good distribution of force. Optionally, the thickness of the material of the hinge is narrower in the radial direction than the thickness of the material of the plurality of protrusions. Optionally, the thickness of the material of the hinge is narrower in the radial direction than the thickness in the radial direction of the material of the ring. These relative dimensions can allow the hinge to be made of the same material as the protrusions and the ring, and can allow the syringe carrier to be made as a single integral component, for example by moulding.

Figure 28:
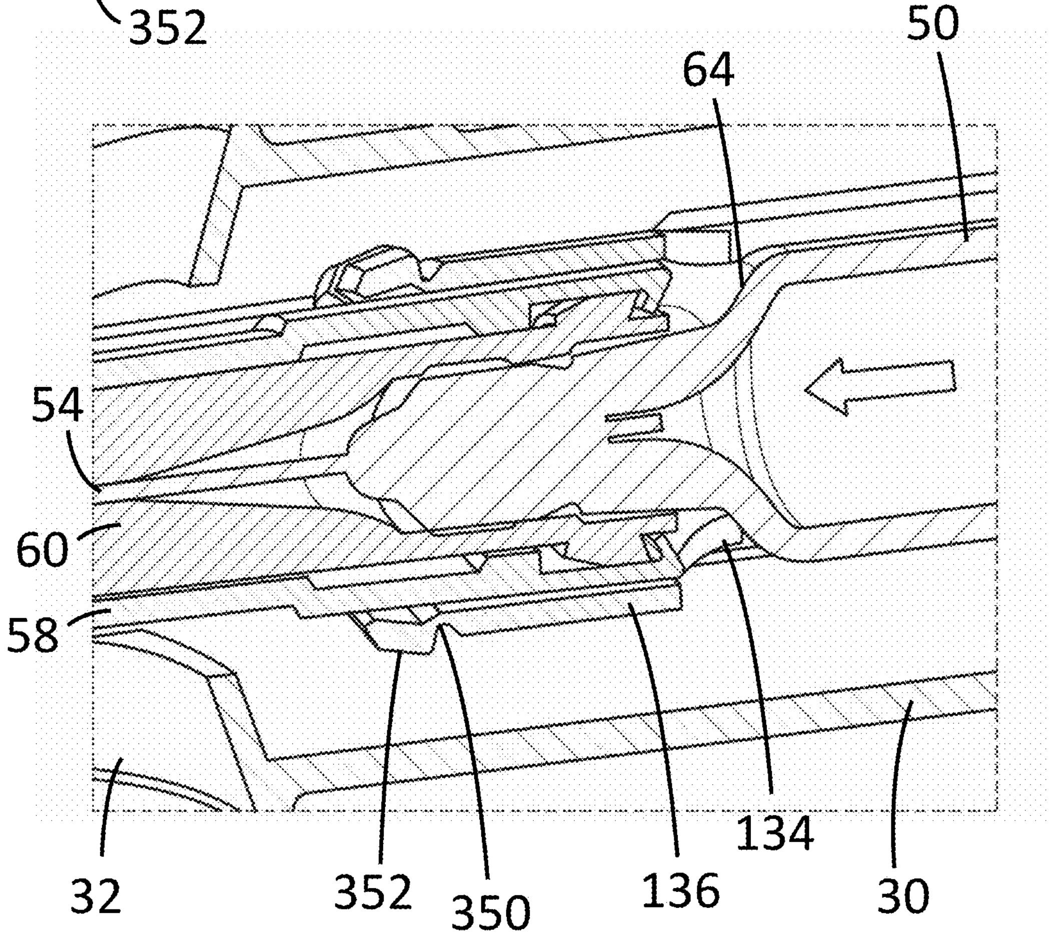
FIGS. 28 and 29 show cross-section views of part of a medicament delivery device with a syringe carrier according to FIG. 27 during assembly.

During assembly, a syringe is first inserted into the syringe carrier, and the syringe and syringe carrier are then inserted into a housing of a medicament delivery device (though these steps can happen in the opposite order as described for other syringe carriers herein, with the syringe carrier being initially placed in a first position inside the housing and being moved to a different final position after the syringe is inserted into the housing and into the syringe carrier). FIG. 28 shows the syringe and syringe carrier being inserted into the housing. In FIG. 28, the syringe carrier is in the housing but is not in its final position. The syringe is also not in its final position, either relative to the housing or relative to the syringe carrier. The protrusions 352 have been forced away from the axis by the RNS 58. From the position shown in FIG. 29, the syringe will continue moving in the proximal direction relative to the syringe carrier, and both the syringe and the syringe carrier will continue moving in the proximal direction relative to the housing.

Figure 29:
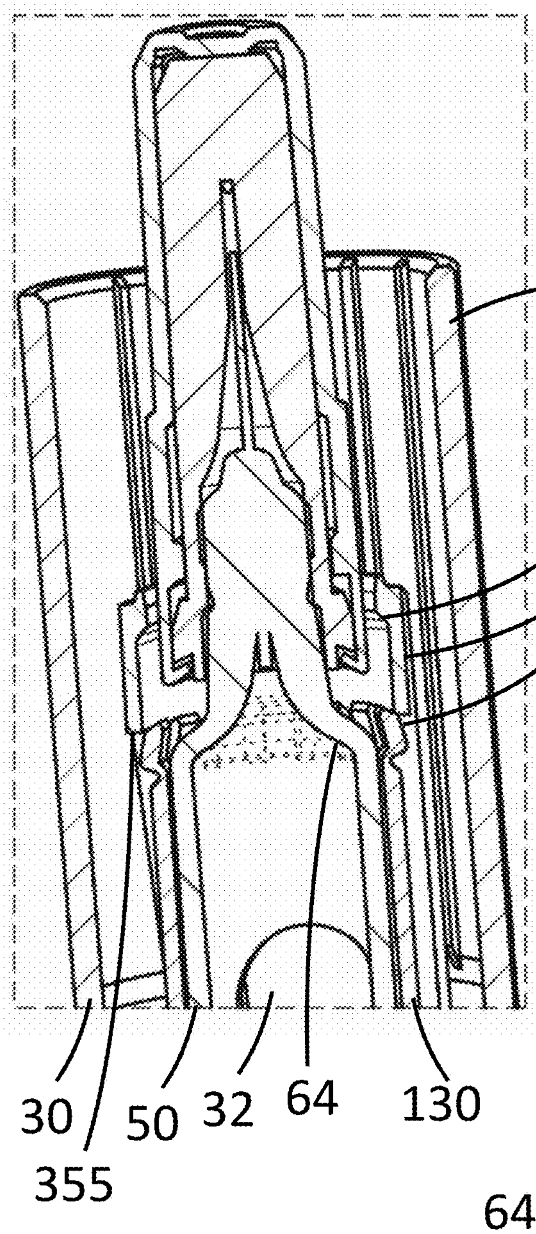
Figure 30:
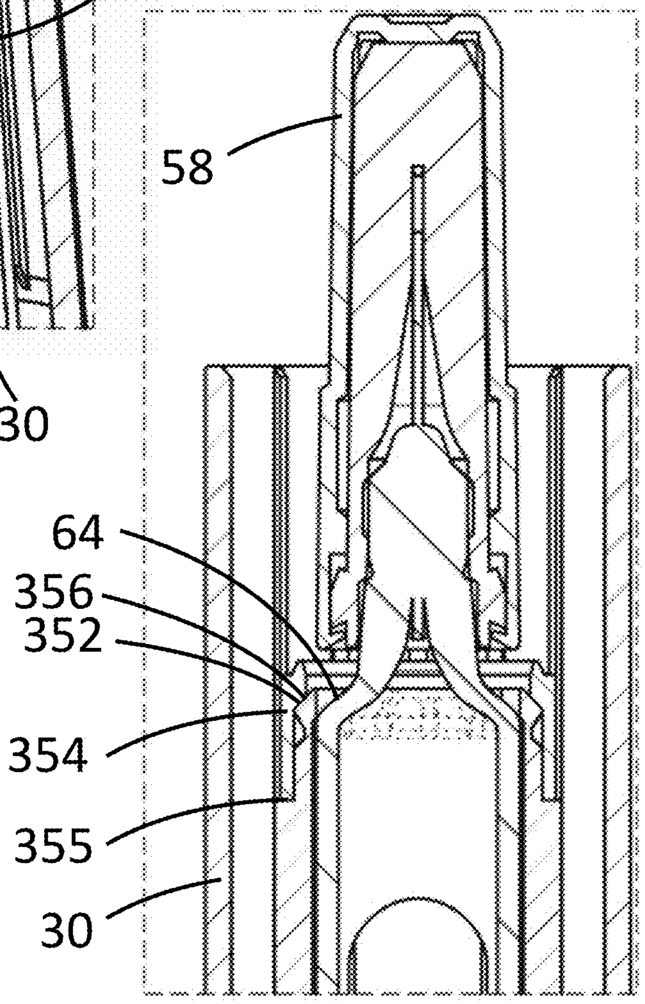
FIG. 30 shows a cross-section view of part of the medicament delivery device of FIG. 28 after assembly has been completed.

FIG. 29 then shows the relative positions of the syringe, syringe carrier and housing as the syringe carrier and syringe reach their final position relative to the housing. Part of the housing (in this case an inner part of the housing—specifically a ring 354 of the housing) engages the flexible protrusions of the syringe carrier as the syringe carrier is pushed in the proximal direction relative to the housing, resulting in the protrusions being pushed towards the axis. As a result, the protrusions end up in a position where they can support the shoulder of the syringe. FIG. 30 shows the final position of the syringe, syringe carrier and housing. The ring 354 has a large enough internal diameter to allow the RNS to pass, but the protrusions 352 cannot pass the ring 354 and are pivoted inwards when they are pushed up against the ring 354. The result is that the protrusions 352 support the shoulder 64 of the syringe, and the ring 354 supports the protrusions 352. In this particular example, a distal surface 355 of the ring (in this case at the distal end of the ring) pushes the protrusion 352 part of the way towards the longitudinal axis in a first step, as shown in FIG. 29, and an inner surface of the ring (in this case a neck 356 of the ring at the proximal end of the ring, where the neck of the ring has a smaller diameter than the rest of the ring) pushes the protrusion the rest of the way towards the longitudinal axis, as shown in FIG. 30. This movement of the protrusion towards the longitudinal axis could alternatively be accomplished in a single step by a single feature of the ring (or more generally by a feature of the housing or of another medicament delivery device component).

The syringe carrier 130 could have differing shapes when initially constructed (i.e. prior to assembly). This initial position is the unbiased position. In a first option for the unbiased position, the proximal end of each of the protrusions 352 is closer to the longitudinal axis than the distal end of each of the plurality of protrusions. As a result, the RNS 58 cannot pass between the protrusions 352 without pushing the protrusions away from the longitudinal axis, as the diameter of the gap between the protrusions is smaller than the diameter of the RNS. This option can be beneficial in that it allows for the protrusions 352 to naturally pivot into the gap between the RNS 58 and the shoulder 64, which can hold the syringe and syringe carrier together during assembly.

The first option outlined above can potentially be disadvantageous as force is required to push the protrusions 352 past the RNS 58. As an alternative second option, the proximal end of each of the protrusions 352 is again closer to the longitudinal axis than the distal end of each of the plurality of protrusions, but in this case the gap between the protrusions is big enough for the RNS to pass without engaging the protrusions. In a third option, the protrusions are again far enough apart that the RNS can pass through the syringe carrier without being engaged by the protrusions 352. In this third option though, the protrusions extend parallel to the longitudinal axis. In the second and third options in particular, engagement of the protrusions with another medicament delivery device component (for example the housing—in particular a ring of an inner part of the housing in the depicted example) during assembly pushes the protrusions towards the axis (in particular the proximal end of the protrusions). This engagement is not essential for the first option outlined above. In all three options, permanent engagement of the protrusions (typically an outer surface of the protrusions) with another medicament delivery device component (for example the housing—in particular a ring of an inner part of the housing in the depicted example) to restrict movement of the protrusions away from the axis can be beneficial, as this can keep the protrusions in place supporting the shoulder even if forces are applied that might otherwise dislodge the protrusions from the gap (such as the device being dropped).

This approach has a couple of potential advantages. For example, the insertion of the syringe into the syringe housing can potentially be performed with no interference (in the second and third options mentioned above). This design can also reduce the accuracy needed when inserting the syringe carrier and syringe into the housing during assembly, as the housing can guide the syringe carrier.

The protrusions 352 could be various shapes. Optionally, the proximal end of the protrusion is shaped to fit the gap (this would depend on the shape of the gap). Preferably, all the protrusions 352 on a given syringe carrier are the same shape. In the example in FIG. 28, the proximal end of the protrusion is tapered. This can help the protrusion to fit in the gap, and can also reduce resistance when the protrusions are engaging the RNS during assembly and/or reduce resistance when the protrusions are engaging the housing during assembly (in particular a ring of an inner part of the housing in the depicted example). In contrast to some other syringe holder designs, the protrusions typically do not need a radially inwardly extending protrusion attached at the proximal end of the protrusion. Instead, the protrusions 352 directly engage the gap.

Optionally, the protrusions are equally spaced around the circumference. this can allow for insertion of the syringe carrier at any rotational position, which can simplify assembly. This can allow for force to be equally spread around the circumference. In general, two or more protrusions could be provided, but preferably at least 6, at least 9, at least 12 or at least 14 protrusions are provided. In particular, preferably between 8 and 16 protrusions are provided, more particularly between 10 and 14 protrusions. The depicted example comprises 12 protrusions.

Another syringe carrier 130 is shown in FIG. 31. In this example, much of the syringe carrier is similar to those described elsewhere herein and the description will not be repeated. The syringe carrier of this example includes a ring 136 spaced apart from the proximal end of the syringe carrier (but still nearer to the proximal end of the syringe carrier than to the distal end of the syringe carrier). The syringe carrier comprises two (although one, three or more could be provided) flexible arms 360 at the proximal end of the syringe carrier, the flexible arms extending in the longitudinal direction. The flexible arms each comprise a protrusion 362 extending from the flexible arm towards the axis. The protrusions on the flexible arms, and therefore the proximal ends of the flexible arms, are flexed away from the axis by the RNS during insertion of a syringe into the syringe carrier, and can then flex back towards the axis after the RNS has passed to support the shoulder of the syringe carrier.

A first example within a related set of examples is shown in FIGS. 32 and 33. In this example, a syringe carrier 130 and a syringe carrier cover 370 are provided. The syringe carrier fits inside the syringe carrier cover. The syringe carrier comprises an arm 372 that is pivotably attached to the proximal end of the syringe carrier. During assembly, the syringe carrier cover and syringe carrier would be arranged as shown in FIG. 32, with the arms of the syringe carrier in an open position and with the arms of the syringe carrier extending beyond the proximal end of the syringe carrier cover. The syringe can then be inserted into the syringe carrier. Once the syringe is inserted, the syringe carrier cover can be pushed in the proximal direction relative to the syringe carrier, resulting in the syringe carrier and syringe carrier cover taking the positions shown in FIG. 33. In particular, pushing the syringe carrier cover in the proximal direction relative to the syringe carrier will pivot the arms from the open position shown in FIG. 32 to the closed position shown in FIG. 33. In the closed position, the arms are closer to one another than in the open position. As a result, the syringe (and particularly the RNS of the syringe) is able to pass the arms when the arms are in the open position, therefore allowing the syringe to be inserted into the syringe carrier, and the syringe is restricted from moving relative to the syringe carrier when the arms are in the closed position, because the arms extend into the gap between the RNS and the shoulder of the medicament holder of the syringe, thereby holding the syringe in place relative to the syringe carrier.

FIGS. 34 and 35 show another example with a similar mechanism during assembly as the example in FIGS. 32 and 33. In this example, the arms 374 are flexible and each include a protrusion 376, and moving the syringe carrier cover in the proximal direction relative to the syringe carrier after the syringe is inserted in the syringe carrier pushes the arms 374 towards one another, thereby pushing the protrusions 376 into the gap between the RNS and the shoulder of the medicament holder of the syringe, thereby holding the syringe in place relative to the syringe carrier.

The resultant sub-assembly comprising a syringe, a syringe carrier and a syringe carrier cover from FIGS. 32 and 33, or FIGS. 34 and 35, can then be inserted into a medicament delivery device. The syringe carrier cover could remain in the device, or could be removed during insertion of the sub-assembly into a medicament delivery device, for example by transferring the syringe and syringe carrier from the syringe carrier cover to a housing of a medicament delivery device, with the structure of the housing subsequently holding the arms in place.

Figure 36:
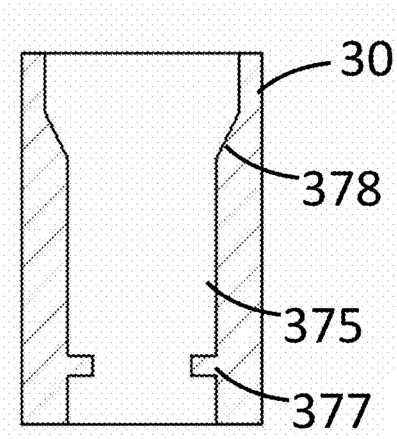
FIGS. 36,37, 38, 39, 40 and 41 show various cross-section views of part of a housing, part of a syringe carrier and a syringe.

FIGS. 36 to 41 show another example of a syringe carrier with flexible arms 374, similar to the syringe carrier shown in FIGS. 34 and 35. In this example, however, a syringe carrier cover is not needed. As shown in FIG. 36, the housing (body) 30 of a medicament delivery device has an internal cavity 375 in which the syringe carrier 130 and syringe 50 are inserted (see FIG. 40, for example). The housing is tubular, and a portion of the housing (typically a distal portion) includes a tapered inner surface 378, so that the diameter of the internal cavity is progressively reduced towards the proximal end of the housing. A protrusion 377 (in this case two protrusions) are provided that protrude into the internal cavity. The protrusions are closer than the tapered inner surface to the proximal end of the housing.

Figure 37:
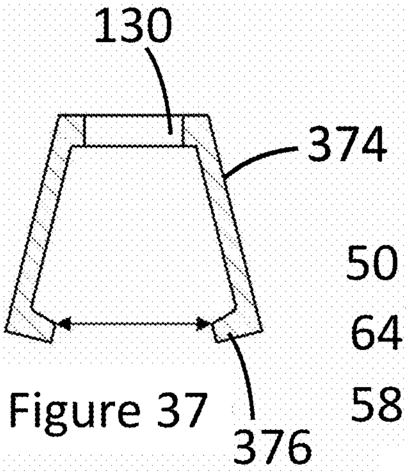
Figure 38:
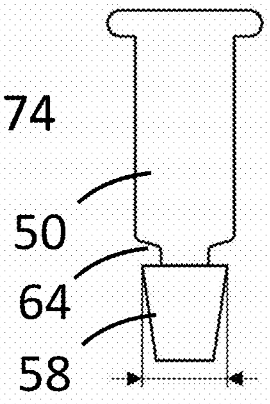
Figure 39:
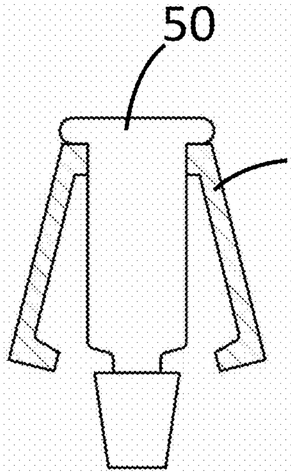
Figure 40:
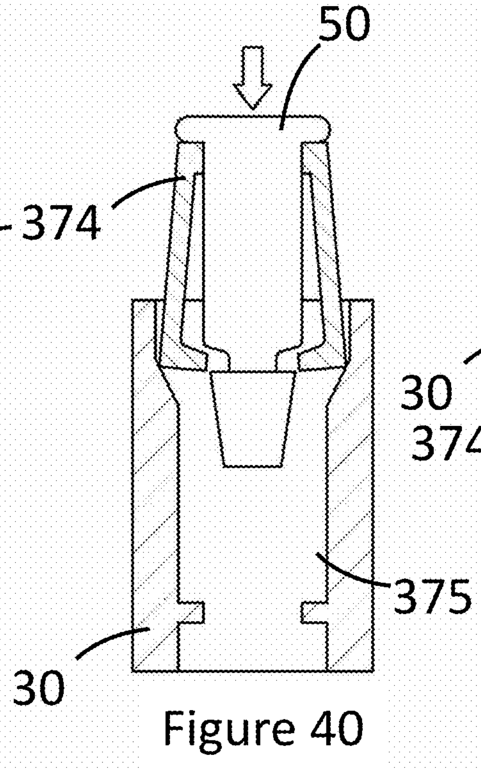
Figure 41:
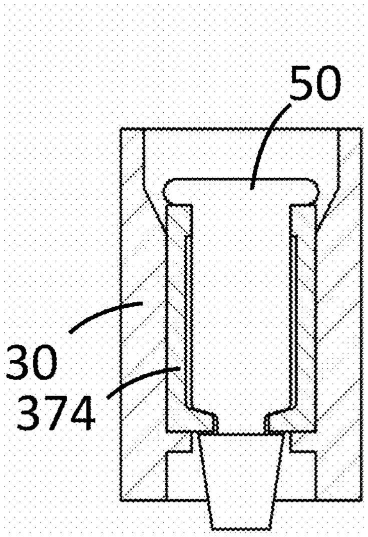

During assembly of a medicament delivery device (or more particularly of a medicament delivery device sub-assembly comprising a syringe, a syringe carrier and a housing), the syringe carrier is initially provided with the arms open as shown in FIG. 37. The syringe (FIG. 38) is then inserted into the syringe carrier (FIG. 39). The syringe carrier and syringe are then inserted into the housing (FIG. 40). As the syringe carrier and syringe move in the proximal direction relative to the housing, the arms of the syringe carrier are pushed towards each other, thereby holding the syringe in place relative to the syringe carrier by pushing the protrusions 376 into the gap between the RNS and the shoulder of the medicament holder of the syringe. The protrusions on the housing limit the proximal motion of the syringe carrier and syringe as shown in FIG. 41. Distal motion of the syringe can optionally be limited by other components of the medicament delivery device.

Another syringe carrier 130 is shown in FIGS. 42 and 43. In this example, much of the syringe carrier is similar to those described elsewhere herein and the description will not be repeated. The syringe carrier comprises a distal portion (a base 132 and two arms 134) and a proximal portion 380. The proximal portion is a tubular section comprising two arms 382. The arms 382 extend in the axial direction. In this example, the arms 382 are attached to the rest of the proximal portion 380 at their distal ends. An alternative in which the arms are instead attached at their proximal ends is shown in FIGS. 47 to 50. With the arms attached at their proximal ends, it may be beneficial to shorten the axial length of the RNS remover to allow more space for the syringe carrier.

Figure 44:
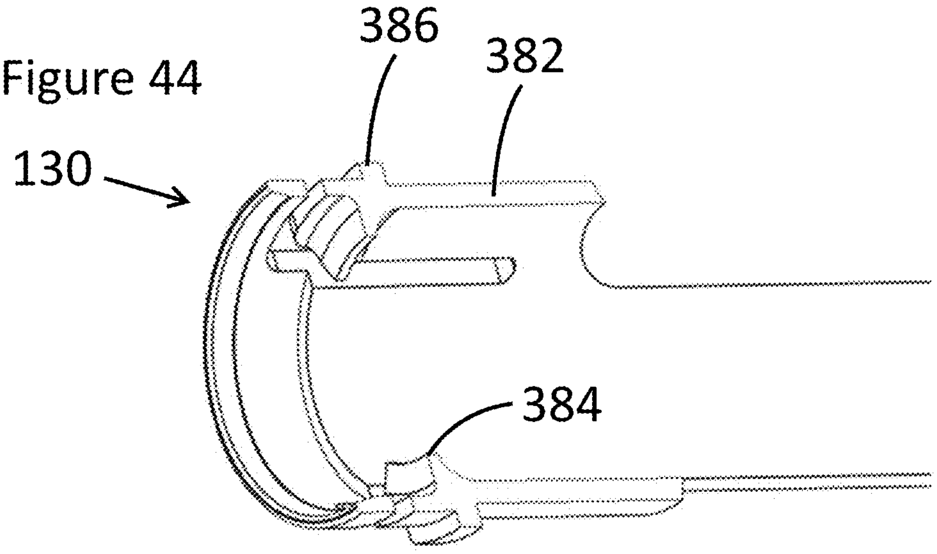
FIG. 44 shows a perspective cross-section view of part of the syringe carrier of FIG. 43.
Figure 45:
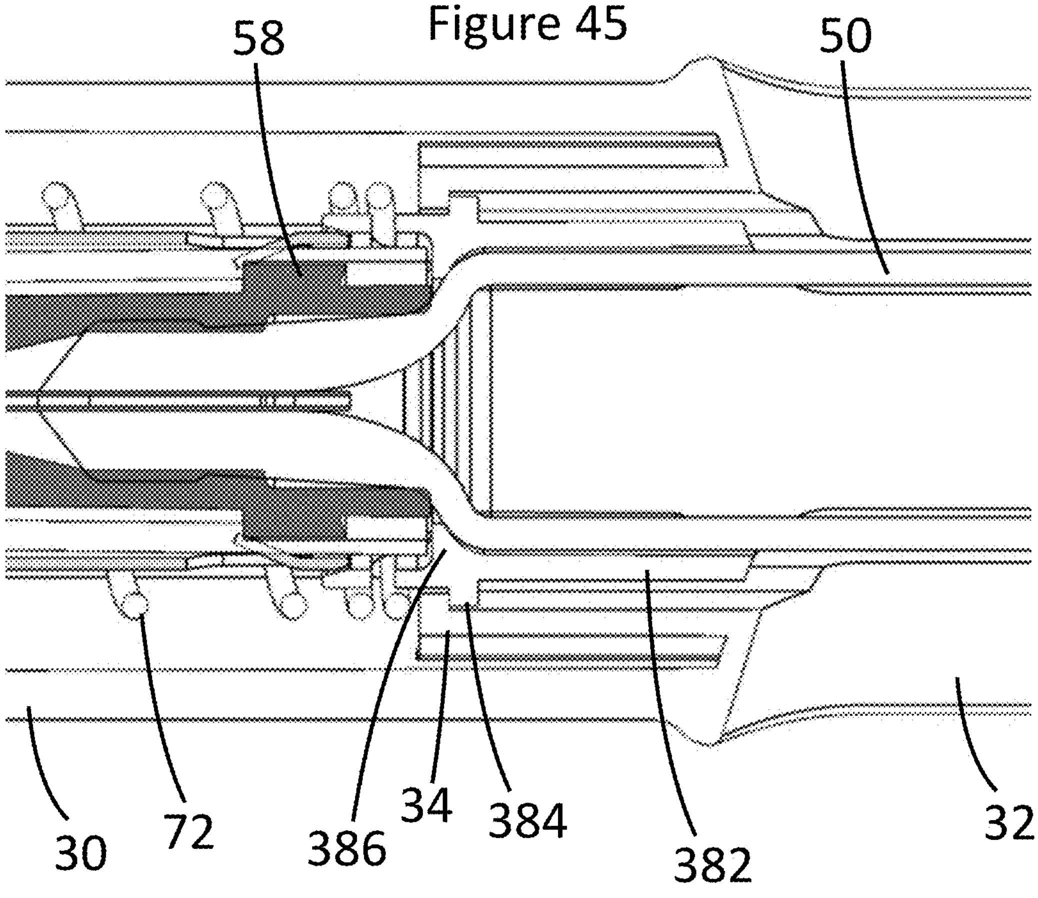
FIG. 45 shows a cross-section view of part of a medicament delivery device comprising the syringe carrier of FIG. 42.

As can be seen more clearly in FIG. 44, each arm comprises an inwardly extending protrusion 384 and an outwardly extending protrusion 386. The inwardly extending protrusion is shaped to engage the gap between the shoulder and the RNS of a syringe. The outwardly extending protrusion is arranged to abut a housing (in this example an inner portion of a housing) of a medicament delivery device. The outwardly extending protrusion is restricted both axially and radially by the housing, as can be seen in FIG. 45, where the final position of the syringe housing inside an example medicament delivery device is shown.

During assembly, a syringe can first be inserted into the syringe carrier before the syringe and the syringe carrier are in their final position in a medicament delivery device. The inwardly extending protrusions will engage the RNS of the syringe and will be pushed away from the axis as the RNS passes. After the RNS has passed the inwardly extending protrusions, the inwardly extending protrusions will move back towards the axis and into the gap between the shoulder and the RNS of the syringe. The syringe and the syringe carrier can then be moved together into their final position inside the housing of the medicament delivery device.

Another syringe carrier 130 is shown in FIGS. 50 to 52. In this example, much of the syringe carrier is similar to those described elsewhere herein and the description will not be repeated. The syringe carrier comprises a tube extending from a proximal end to a distal end. In contrast to other syringe carriers described herein, the syringe carrier does not include arms 134 (this approach could also be used for the other syringe carriers described herein). To allow for a drug in a syringe inside the syringe carrier to be seen, part or all of the syringe carrier can be made of a transparent material.

The syringe carrier 130 comprises two arms 390 extending at the proximal end of the syringe carrier. The arms are flexible. The arms extend in the circumferential direction. The arms 390 each comprise an inwardly extending protrusion 392. One end of each arm is attached to the rest of the syringe carrier, and the other end of each arm is free to move in the radial direction. When the syringe carrier is in a relaxed state, the protrusions 392 are not far enough apart for an RNS of a syringe to pass between the protrusions. As a result, during assembly when the syringe is inserted into the syringe carrier, the RNS pushes the protrusions apart, thereby pushing the arms outwards (this is the position shown in FIGS. 50 to 52—with the arms of the syringe carrier pushed outwards). Once the RNS has passed the protrusions 392, the protrusions can move back towards one another, with the result that the protrusions protrude into the gap between the RNS and the shoulder of the syringe. The syringe and syringe carrier can then be moved to their final position within a medicament delivery device. Optionally, a feature of the medicament delivery device (for example an inner surface of a housing) restricts movement of the arms 390 once the syringe and syringe carrier are in the final position within the medicament delivery device—this can stop the protrusions 392 from subsequently leaving the gap between the RNS and the shoulder of the syringe.

The examples herein focus on autoinjectors, but the examples described herein could be implemented in other medicament delivery devices more generally, such as in pen injectors. Some of the examples herein focus on 1 ml syringes, but the designs described herein could also be used on other volumes and other types of medicament container, for example a syringe without an attached needle rather than a syringe with an attached needle. An example of an autoinjector 10 that could comprise the syringe carriers described herein is shown in FIG. 53. The example autoinjector extends along an axis 12 in an axial direction 13 between a distal end 15 and a proximal end 14, with a radial direction 17 and a circumferential direction 16 also depicted for reference. A housing (or body) 30 and a cap 90 of the autoinjector can be seen, along with an optional window 32 in the housing. The autoinjector can house a syringe. The autoinjector typically includes features such as a powerpack and a needle guard inside the housing. The shape of the housing and of the cap could be varied from those shown in the example—for example, the housing could be triangular in cross section perpendicular to the axis rather than circular, could be an irregularly-shaped tube rather than a cylinder, and/or the housing could be two or more components rather than a single component. The autoinjector shown does not have an activation button, though one could be provided (i.e. a three-step autoinjector rather than a two-step autoinjector).

FIGS. 54 and 55 show an example of a syringe for reference. This particular syringe 50 comprises a medicament holder (medicament container) 52, a needle 54, a stopper 56, a rigid needle shield (RNS) 58, a flexible needle shield (FNS) 60, a flange 62 and a shoulder 64. The syringe extends from a proximal end 14 to a distal end 15. The medicament holder 52 is tubular (specifically cylindrical in this example), with the flange 62 at the distal end of the medicament holder 52 and the needle 54 at the proximal end of the medicament holder 52. The stopper 56 is in the medicament holder 52. The flexible needle shield 60 extends around the needle 54, and the rigid needle shield 58 extends around the flexible needle shield. The shoulder 64 is the proximal end of the medicament holder 52. One particular example syringe is described here, but other syringes could be used. For example, a needle 54 is included in examples described herein, but other medicament delivery members such as jet injectors could alternatively be used, or the needle could be provided separately rather than as an integral part of the syringe. The flange 62 is optional. A needle shield comprising a rigid needle shield 58 and a flexible needle shield 60 is included in examples described herein, but the examples described herein could be used with needle shields without a flexible needle shield or even entirely without a needle shield, although the examples described herein can be particularly beneficial when used with syringes with an RNS. The syringe could be various sizes, including but not limited to 1 ml and 2.25 ml.

Example mechanical powerpacks are described herein (for example the powerpack shown in FIG. 13), but other types of powerpack could be used instead, for example an electrically powered powerpack or a gas-powered powerpack. The example autoinjector 10 shown in FIG. 13 comprises a powerpack comprising a rear housing 80 and a rotator 82, a cap 90 comprising a cap housing 92 and a RNS remover 94, a syringe 50, a syringe carrier 130, an optional needle guard 70, an optional needle guard spring 72, a housing 30, and a plunger rod 100 and plunger rod spring (not shown). Another example of a device in which syringe carriers as described herein could be used is provided in WO2011/123024, which is hereby incorporated by reference.

A base 132 is described herein. Typically, the base is depicted as the distal portion of the syringe carrier, but could alternatively be spaced apart in the axial direction from the distal end of the syringe carrier.

Arms 134 are described herein. Most (though not all) of the examples herein use two arms, although in the examples with two arms, one, three or more arms could alternatively be provided. Similarly, other features that are provided (arms, protrusions, cut-outs, recesses and the like) can generally be provided in a quantity different to the specific number described in the examples given.

Many of the syringe carriers described herein comprise some kind of optional protrusion or rib. For example, a number of the examples, including the syringe carriers shown in FIGS. 2, 6 and 15, comprise two ribs 138, four second ribs 139 and two protrusions 140. The ribs 138 extend in the longitudinal direction, with the proximal end of each rib 138 attached to an arm 134 and the distal end of each rib 138 attached to the base 132. The second ribs 139 extend in the longitudinal direction. A second rib 139 is arranged on each side of each arm 134 in the circumferential direction. The protrusions 140 are attached to the base 132. Another optional feature is a distal flange 148, which is also present in many of the syringe carriers described herein. The flange 148 is attached to the base 132 and extends in the radial direction away from the axis and extends in the circumferential direction around the base. These ribs, protrusions and flanges can provide various advantages, including helping to align the syringe carrier relative to other features during assembly, maintaining rigidity of the syringe carrier, and/or fixing the position of the syringe carrier relative to other components of a medicament delivery device in a completed device. Whilst these protrusions 140, ribs 138, 139 and flanges 148 are depicted as having a particular shape, these shapes could be varied depending on factors such as the desired rigidity and on the shape of other components within a particular design of medicament delivery device.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component. The circumferential direction describes a direction extending around the axis, so around the circumference of a device or component, and the radial direction extends perpendicular to the axis.

Similarly, the terms "transverse", "transversal" and "transversally" refer to a direction generally perpendicular to the longitudinal direction.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

Various modifications to the embodiments described are possible and will occur to those skilled in the art without departing from the present disclosure which is defined by the following claims.

Certain aspects of the present disclosure are outlined in the following numbered clauses.

1. A medicament delivery device sub-assembly extending along a longitudinal axis (12) from a proximal end (14) to a distal end, the medicament delivery device sub-assembly comprising a tubular housing (30), a tubular syringe carrier (130) inside the tubular housing (30) and a syringe (50) inside the syringe carrier (130),
   wherein the syringe (50) comprises a needle shield (58, 60) and a medicament container (52) comprising a shoulder (64),
   wherein the tubular housing (30) comprises a flexible arm (320) extending in the axial direction (13) relative to the longitudinal axis (12), the flexible arm (320) comprising an inwardly extending protrusion (322),
   wherein the inwardly extending protrusion (322) is arranged in a gap between the shoulder (64) and the needle shield (58, 60),
   wherein the syringe carrier (130) comprises a proximal portion and a distal portion, and the proximal portion is arranged adjacent to the flexible arm (320) of the tubular housing (30) so that movement of the flexible arm (320) of the tubular housing (30) in a radial direction (17) relative to the longitudinal axis (12) is restricted by the proximal portion of the syringe carrier (130).
2. The medicament delivery device sub-assembly of clause 1, wherein the syringe carrier comprises an axially flexible structure that allows the syringe carrier to shorten its length in the axial direction during assembly.
3. The medicament delivery device sub-assembly of clause 1 or 2, wherein the proximal portion of the syringe carrier comprises a ring.
4. The medicament delivery device of clause 2 or 3, wherein the axially flexible structure is attached to the distal end of the ring.
5. The medicament delivery device sub-assembly of clause 1, wherein the proximal portion of the syringe carrier comprises an arm extending in the axial direction relative to the longitudinal axis.
6. The medicament delivery device sub-assembly of clause 5, wherein the arm of the syringe carrier is inflexible.
7. The medicament delivery device sub-assembly of clause 5 or 6, wherein a distal end of the arm is attached to a ring.
8. The medicament delivery device sub-assembly of any previous clause, wherein the distal portion of the syringe comprises a base and an arm, and the proximal portion of the syringe is attached to the proximal end of the arm.
9. The medicament delivery device sub-assembly of clause 8, wherein the base is tubular.
10. The medicament delivery device sub-assembly of any previous clause, wherein the needle shield comprises a rigid needle shield, and wherein the inwardly extending protrusion is arranged in a gap between the shoulder and the rigid needle shield.
11. The medicament delivery device sub-assembly of any previous clause, wherein the flexible arm of the housing is attached to the rest of the housing at the distal end of the flexible arm.
12. A medicament delivery device sub-assembly comprising:
   a housing extending along an axis from a proximal end to a distal end, the housing describing a tubular space within the housing, the housing comprising an arm extending into the tubular space,
   a syringe carrier arranged inside the tubular housing, the syringe carrier comprising an arm, and
   a syringe arranged inside the syringe carrier,
   wherein the arm of the housing comprises a first surface facing towards the distal end of the housing, and wherein a shoulder of the syringe is arranged adjacent to the first surface,
   wherein the arm of the housing comprises a second surface facing away from the axis, and wherein the arm of the housing is adjacent to the arm of the syringe carrier so that the arm of the housing is restricted from moving away from the axis by the arm of the syringe carrier.

13. The medicament delivery device sub-assembly of clause 12, wherein the arm of the syringe carrier extends in the proximal direction at the proximal end of the syringe carrier.
14. The medicament delivery device sub-assembly of clause 12 or 13, wherein the first surface is on a protrusion of the arm of the housing.
15. The medicament delivery device sub-assembly of any of clauses 12 to 14, wherein the protrusion of the arm of the housing extends from the arm towards the axis.
16. The medicament delivery device sub-assembly of any of clauses 12 to 15, wherein the syringe carrier is tubular.
17. A method of assembling a medicament delivery device sub-assembly according to any of clauses 1 to 16, the method comprising the steps of:
  providing the housing, the syringe carrier and the syringe; and inserting the syringe carrier and the syringe into the housing.
18. The method of clause 17, wherein the step of inserting the syringe carrier and the syringe into the housing comprises, in either order, the steps of
  inserting the syringe carrier into the housing and
  inserting the syringe into the syringe carrier.
19. The method of clause 17, wherein the step of inserting the syringe carrier and the syringe into the housing comprises the following steps in the following order:
  inserting the syringe carrier into a first position in the housing;
  inserting the syringe into the syringe carrier, either before or after inserting the syringe carrier into the first position in the housing; and
  moving the syringe carrier from the first position to a final position in the housing, wherein the final position in the housing is closer to the proximal end than the first position.
20. The method of any of clauses 17 to 19, wherein the syringe carrier and the syringe are both inserted into a distal end of the housing.
21. The method of any of clauses 17 to 20, wherein the length of the syringe carrier varies during assembly.
22. The method of clause 21, wherein the length of the syringe carrier is reduced during assembly by interaction of a proximal end of the syringe carrier with an arm of the housing.
23. The method of any of clauses 17 to 22, wherein a needle shield of the syringe pushes an arm of the housing away from the longitudinal axis during assembly, and wherein the arm of the housing limits the proximal movement of the proximal portion of the syringe carrier whilst the arm is pushed away from the longitudinal axis.
24. A syringe carrier for a medicament delivery device, the syringe carrier extending along a longitudinal axis from a proximal end to a distal end, the syringe carrier comprising:
  a plurality of arms extending in the axial direction at the proximal end of the syringe carrier, wherein the arms are spaced apart in the circumferential direction relative to the longitudinal axis around the proximal end of the syringe carrier; and
  a plurality of flexible strips, the plurality of flexible strips describing at least part of a ring in the circumferential direction around the longitudinal axis, wherein each one of the plurality of strips extends in the circumferential direction from a first end attached to one of the plurality of arms to a second end attached to another of the plurality of arms,
  wherein each of the plurality of flexible strips describes an arc, and the middle of the arc is closer to the longitudinal axis than the first end and the second end.
25. The syringe carrier of clause 24, wherein the plurality of arms comprises four to six arms.
26. The syringe carrier of clause 24 or 25, wherein the number of flexible strips is the same as the number of arms.
27. The syringe carrier of any of clauses 24 to 26, wherein the plurality of arms are inflexible.
28. The syringe carrier of any of clauses 24 to 27, wherein the plurality of flexible strips are configured to flex outwards when a syringe is inserted into the syringe carrier.
29. The syringe carrier of any of clauses 24 to 28, wherein the plurality of arms each extend from a proximal end to a distal end,
  wherein the distal end of each of the plurality of arms is attached to the rest of the syringe carrier, and
  wherein the plurality of arms are attached to the plurality of flexible strips at the proximal end of the arms.
30. The syringe carrier of any of clauses 24 to 29, wherein the syringe carrier comprises a tubular base at the distal end.
31. The syringe carrier of any of clauses 24 to 30, wherein the plurality of flexible strips are arranged to flex from the position where the middle of the arc is closer to the longitudinal axis than the first end and the second end to a position where the middle of the arc is further from the longitudinal axis than the first end and the second end to allow a needle shield of a syringe to pass between the plurality of flexible strips.
32. The syringe carrier of any of clauses 24 to 31, wherein the arms and the strips alternate in the circumferential direction.
33. The syringe carrier of any of clauses 24 to 32, wherein the plurality of flexible strips form a complete ring in the circumferential direction around the longitudinal axis.
34. The syringe carrier of any of clauses 24 to 33, wherein a distal end of each of the plurality of arms is attached to a second ring.
35. The syringe carrier of any of clauses 24 to 34, wherein the syringe carrier is tubular.
36. A medicament delivery device sub-assembly comprising a housing, a syringe carrier according to any of clauses 24 to 35 inside the housing, and a syringe inside the syringe carrier, wherein at least part of each of the plurality of flexible strips is in a gap between a needle shield of the syringe and a shoulder of the syringe.
37. The medicament delivery device sub-assembly of clause 36, wherein a portion of the housing restricts movement away from the longitudinal axis by the plurality of flexible strips.
38. A syringe carrier for a medicament delivery device, wherein the syringe carrier comprises an expandable ring.
  wherein the expandable ring comprises one or more hinges spaced around the circumference of the expandable ring.
  wherein the ring comprises two or more hinges, and wherein the hinges are convexly curved strips.

39. A method of assembling a medicament delivery device sub-assembly comprising a syringe carrier according to any of clauses 24 to 35 or a medicament delivery device sub-assembly according to clause 36 or 37, the method comprising the steps of:
providing a housing, the syringe carrier and a syringe; and
inserting the syringe carrier and the syringe into the housing.
40. The method of clause 39, wherein the step of inserting the syringe carrier and the syringe into the housing comprises, in either order, the steps of
inserting the syringe carrier into the housing and
inserting the syringe into the syringe carrier
41. The method of clause 39, wherein the step of inserting the syringe carrier and the syringe into the housing comprises the following steps in the following order:
inserting the syringe carrier into a first position in the housing;
inserting the syringe into the syringe carrier, either before or after inserting the syringe carrier into the first position in the housing; and
moving the syringe carrier from the first position to a final position in the housing, wherein the final position in the housing is closer to the proximal end than the first position.
42. The method of any of clauses 39 to 41, wherein during the method of assembling the medicament delivery device sub-assembly, at least part of each of the plurality of protrusions is inserted into a gap between a needle shield of the syringe and a shoulder of the syringe.
43. A syringe carrier for a medicament delivery device, wherein the syringe carrier extends along a longitudinal axis, wherein the syringe carrier comprises a plurality of protrusions extending in the axial direction relative to the longitudinal axis from a proximal end of the syringe carrier, the plurality of protrusions each extending from a proximal end to a distal end, wherein the distal end of each of the plurality of protrusions is attached to the rest of the syringe carrier by a hinge and wherein each of the plurality of protrusions is pivotable about the hinge so that the plurality of protrusions can move from a first position to a second position,
wherein in the second position, the proximal end of each of the plurality of protrusions is closer to the longitudinal axis than the distal end of each of the plurality of protrusions, so that the plurality of protrusions can support a syringe inside the syringe carrier, and
wherein the proximal ends of the plurality of protrusions are further from the longitudinal axis in the first position than in the second position.
44. The syringe carrier of clause 43, wherein the first position is a relaxed position and the second position is a biased position.
45. The syringe carrier of clause 43 or 44, wherein the plurality of protrusions are equally spaced around the circumference.
46. The syringe carrier of any of clauses 43 to 45, wherein each of the plurality of protrusions does not comprise a radially inwardly extending protrusion extending from the protrusion.
47. The syringe carrier of any of clauses 43 to 46, wherein the thickness of the material of the hinge is narrower in the radial direction than the thickness of the material of the plurality of protrusions.
48. The syringe carrier of any of clauses 43 to 47, wherein the distal end of each of the plurality of protrusions is attached by the hinge to a ring of the syringe carrier, and wherein the ring is attached to a base by at least one arm.
49. The syringe carrier of clause 48, wherein the thickness of the material of the hinge is narrower in the radial direction than the thickness in the radial direction of the material of the plurality of protrusions and the thickness in the radial direction of the material of the ring.
50. The syringe carrier of any of clauses 43 to 49, wherein the plurality of protrusions comprises at least 9 protrusions, and preferably comprises between 10 and 14 protrusions.
51. The syringe carrier of any of clauses 43 to 50, wherein the protrusions are flexible.
52. The syringe carrier of any of clauses 43 to 51, wherein the proximal end of each of the plurality of protrusions is tapered.
53. A medicament delivery device sub-assembly comprising a housing, a syringe carrier according to any of clauses 43 to 52 inside the housing, and a syringe inside the syringe carrier, wherein at least part of each of the plurality of protrusions is in a gap between a needle shield of the syringe and a shoulder of the syringe.
54. The medicament delivery device sub-assembly of clause 53, wherein at least half of the length of each of the plurality of protrusions is in a gap between a needle shield of the syringe and a shoulder of the syringe.
55. The medicament delivery device sub-assembly of clause 53 or 54, wherein a portion of the housing restricts movement away from the longitudinal axis by the plurality of protrusions.
56. The medicament delivery device sub-assembly of clause 55, wherein the portion of the housing is a ring of an inner portion of the housing.
57. A method of assembling a medicament delivery device sub-assembly comprising a syringe carrier according to any one of clauses 43 to 52 or a medicament delivery device sub-assembly according to any of clauses 53 to 56, the method comprising the steps of:
providing a housing, the syringe carrier and a syringe; and
inserting the syringe carrier and the syringe into the housing.
58. The method of clause 57, wherein the step of inserting the syringe carrier and the syringe into the housing comprises, in either order, the steps of
inserting the syringe carrier into the housing and
inserting the syringe into the syringe carrier.
59. The method of clause 57, wherein the step of inserting the syringe carrier and the syringe into the housing comprises the following steps in the following order:
inserting the syringe carrier into a first position in the housing;
inserting the syringe into the syringe carrier, either before or after inserting the syringe carrier into the first position in the housing; and
moving the syringe carrier from the first position to a final position in the housing, wherein the final position in the housing is closer to the proximal end than the first position.
60. The method of any of clause 59, wherein when the syringe carrier is moved to the final position in the housing, the plurality of protrusions are pushed towards the longitudinal axis to support a shoulder of the syringe.

61. A medicament delivery device comprising the syringe carrier of any one of clauses 24 to 35, 38, or 43 to 52, or a medicament delivery device sub-assembly of any one of clauses 1 to 16, 36, 37, or 53 to 56.
62. The medicament delivery device of clause 61, in which the medicament delivery device is an autoinjector.
63. A method of assembling a medicament delivery device, comprising the method of assembling a medicament delivery device sub-assembly of any one of clauses 17 to 23, 39 to 42 or 57 to 60.
64. The method of clause 63, in which the method of assembling a medicament delivery device is a method of assembling an autoinjector.

The invention claimed is:

1. A medicament delivery device sub-assembly extending along a longitudinal axis from a proximal end to a distal end, the medicament delivery device sub-assembly comprising a tubular housing, a tubular syringe carrier inside the tubular housing and a syringe inside the syringe carrier, wherein the syringe comprises a needle shield and a medicament container comprising a shoulder, wherein the tubular housing comprises a flexible arm extending in the axial direction relative to the longitudinal axis, the flexible arm comprising an inwardly extending protrusion, wherein the inwardly extending protrusion is arranged in a gap between the shoulder and the needle shield, wherein the syringe carrier comprises a proximal portion and a distal portion, and the proximal portion is arranged adjacent to the flexible arm of the tubular housing so that movement of the flexible arm of the tubular housing in a radial direction relative to the longitudinal axis is restricted by the proximal portion of the syringe carrier.

2. The medicament delivery device sub-assembly of claim 1, wherein the syringe carrier comprises an axially flexible structure that allows the syringe carrier to shorten its length in the axial direction during assembly.

3. The medicament delivery device sub-assembly of claim 1, wherein the proximal portion of the syringe carrier comprises a ring.

4. The medicament delivery device sub-assembly of claim 1, wherein the proximal portion of the syringe carrier comprises an arm extending in the axial direction.

5. The medicament delivery device sub-assembly of claim 1, wherein the needle shield comprises a rigid needle shield, and wherein the inwardly extending protrusion is arranged in a gap between the shoulder and the rigid needle shield.

6. The medicament delivery device sub-assembly of claim 1, wherein the distal portion of the syringe carrier comprises a base and an arm, and the proximal portion of the syringe carrier is attached to a proximal end of the arm.

7. The medicament delivery device sub-assembly of claim 6, wherein the base is tubular.

* * * * *